(12) United States Patent
Mitalipova et al.

(10) Patent No.: US 7,432,104 B2
(45) Date of Patent: Oct. 7, 2008

(54) METHODS FOR THE CULTURE OF HUMAN EMBRYONIC STEM CELLS ON HUMAN FEEDER CELLS

(75) Inventors: Maisam Mitalipova, Athens, GA (US); Ian Lyons, Athens, GA (US)

(73) Assignee: BresGen Inc., Athens, GA (US)

( * ) Notice: Subject to any disclaimer, the term of this patent is extended or adjusted under 35 U.S.C. 154(b) by 458 days.

(21) Appl. No.: 10/486,408

(22) PCT Filed: Aug. 6, 2002

(86) PCT No.: PCT/US02/25102

§ 371 (c)(1),
(2), (4) Date: Oct. 4, 2004

(87) PCT Pub. No.: WO03/014313

PCT Pub. Date: Feb. 20, 2003

(65) Prior Publication Data

US 2005/0037488 A1 Feb. 17, 2005

(51) Int. Cl.
*C12N 5/02* (2006.01)
*C12N 5/08* (2006.01)

(52) U.S. Cl. .................... 435/373; 435/366; 435/377

(58) Field of Classification Search .............. 435/373, 435/375, 377
See application file for complete search history.

(56) References Cited

U.S. PATENT DOCUMENTS

| | | | |
|---|---|---|---|
| 5,690,926 A | * | 11/1997 | Hogan .................. 424/93.1 |
| 6,200,806 B1 | | 3/2001 | Thomson |
| 2002/0013704 A1 | | 1/2002 | Finney |
| 2002/0022268 A1 | | 2/2002 | Xu et al. |
| 2002/0072117 A1 | | 6/2002 | Xu et al. |
| 2002/0081724 A1 | | 6/2002 | Carpenter et al. |

FOREIGN PATENT DOCUMENTS

| | | |
|---|---|---|
| AU | 751321 | 7/2001 |
| WO | WO 96/22362 | 7/1996 |
| WO | WO 99/53021 | 10/1999 |
| WO | WO 00/27995 | 5/2000 |
| WO | WO 01/51616 A3 | 7/2001 |
| WO | WO 03/014313 A2 | 2/2003 |

OTHER PUBLICATIONS

Eiges et al. A Molecular View on Pluriopotent Stem Cells, FEBS Letters. 2002, vol. 529, pp. 135-141.*
ATCC Catalog, 1994, pp. 171 and 236.*

* cited by examiner

*Primary Examiner*—Deborah Crouch
(74) *Attorney, Agent, or Firm*—Sutherland Asbill & Brennan LLP

(57) ABSTRACT

Methods and cell culture medium for the generation of human pluripotent embryonic stem cells are disclosed. Human embryonic stem cells are cultured with human granulosa feeder cells, muscle cells, Fallopian ductal epithelial cells, bone marrow stromal cells, and skin fibroblasts and the embryonic stem cells maintain their pluripotent phenotype. The human pluripotent embryonic stem cells can be cultured without feeder cells, and in the presence of supplemental growth factors. The human pluripotent embryonic stem cells can be alternatively cultured with conditioned medium obtained from a cell culture capable of maintaining human embryonic stem cells in a pluripotent state, wherein the cell culture is a human granulosa cell culture.

21 Claims, 4 Drawing Sheets

A

B

A

B

C

D

E

F

G

H

I

J

A

B

C

D

```
SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctcctggagg gccaggaatc                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccacatcggc ctgtgtatat                                              20

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgaaggtcgg agtcaacgga tttggt                                       26

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
catgtgggcc atgaggtcca ccac                                         24
```

METHODS FOR THE CULTURE OF HUMAN EMBRYONIC STEM CELLS ON HUMAN FEEDER CELLS

FIELD OF THE INVENTION

This invention relates generally to the isolation, maintenance, and use of stem cell cultures. Specifically, the field of the present invention is human embryonic stem cell culture system using a human feeder cell.

BACKGROUND

Embryonic stem cells, referred to as ES cells, are derived from the inner cell mass (ICM) of fertilized eggs in blastocyst phase, and can be cultured and maintained in vitro while being kept in an undifferentiated state. ES cells are pluripotent, possessing the capability of developing into any organ or tissue type or, at least potentially, into a complete embryo. For example, ES cells can differentiate and give rise to a succession of mature functional cells. Differentiation has been shown in tissue culture and in vivo.

An important application of human ES cells is their use in cell therapy: the treatment of symptoms, diseases, conditions, and disabilities with ES cell derived replacement cells and tissues. Many diseases and disorders result from disruption of cellular function or destruction of tissues of the body. A wide spectrum of diseases may be treated based upon both the possession of a population of cells having multi-lineage potential and an understanding of the mechanisms that regulate embryonic cell development. Pluripotent stem cells that are stimulated in vitro to develop into specialized cells offer the possibility of a renewable source of replacement cells and tissue to treat numerous diseases, conditions, and disabilities. Some of these diseases, conditions, and disabilities include but are not limited to Parkinson's and Alzheimer's diseases and other neurodegenerative disorders, spinal cord injuries, stroke, macular degeneration, burns, liver failure, heart disease, diabetes, Duchenne's muscular dystrophy, osteogenesis imperfecta, osteoarthritis, rheumatoid arthritis, anemia, leukemia, breast cancer and other solid tumors, and AIDS.

ES cells have been derived from mouse (Evans and Kaufman, Nature 292:154-156, 1981; Martin, PNAS USA 78:7634-7639, 1981), hamster (Doetschmann et al., Dev. Biol., 127:224-227, 1999), sheep (Handyside et al., Roux's Arch. Dev. Biol., 198:48-55, 1987; Notarianni et al., J. Reprod. Fertil., 43:255-260, 1991; Piedrahita et al., Theriogenology, 34:879-901, 1990), cow (Evans et al., Theriogenology, 33:125-128, 1990), rabbit (Giles et al., Mol. Reprod. Dev., 36:130-138, 1993), mink (Sukoyan et al., Mol. Reprod. Devl, 36:148-158, 1993) and pig (Piedrahita et al., Theriogenology, 29:286, 1988; Evans et al., supra, 1990; Notarianni et al., J. Reprod. Fertil., Suppl. 41:51-56, 1990). Recently, the derivation of human ES cells has been reported (Thomson et al., Science, 282:1145-1147, 1998; Shamblott, et al, Proc. Natl. Acad. Sci. USA, 95:13726-13731, 1998; Reubinoff et al., Nature Biotechnology 18:399-404, 2000 (published erratum Nature Biotechnology 18:559, 2000)).

Human ES cells have been isolated from two different tissue sources, however, the characteristics of the derived ES and embryonic germ (EG) cells are very similar (reviewed in Pera et al., J. Cell Science, 113:5-10, 2000). Thomson et al. isolated ES cells from the ICM of surplus human blastocysts that had been donated from fertility clinics (Thomson et al., supra, 1998), while Shamblott et al. isolated stem cells from the gonadal tissues of terminated pregnancies (Shamblott et al., supra, 1998). In neither case were the blastocysts or embryos created for the purpose of research.

The ES cell isolated by Thomson et al., and the embryonic germ (EG) cell derived by Shamblott et al. are reported to share certain characteristics: the cells originate from a pluripotent cell population; they maintain a normal karyotype in vitro; they are immortal and can be propagated indefinitely in the embryonic state; and are capable of spontaneous differentiation into somatic cells representative of all three embryonic germ layers in teratomas or in vitro (reviewed in Pera et al., supra, 2000).

The culture conditions for the human ES and EG cells differ from the culture conditions for the mouse ES cell. Mouse ES cells are typically derived using fibroblast feeder layers. The fibroblast feeder layers typically are either STO fibroblasts, a transformed cell line, or more often, the mouse ES cell is co-cultured with a primary culture of mouse embryonic fibroblasts (MEFs). These cultures are typically supplemented with leukemia inhibitory factor (LIF). The mouse ES culture medium may alternatively be supplemented with other growth factors that prevent differentiation. Examples of such growth factors are OSM, CNTF, IL-6 in combination with soluble IL-6 R, or other cytokines that signal through the gp130 pathway.

Mouse ES cells remain undifferentiated indefinitely in the presence of an embryonic fibroblast feeder layer. Similarly, it is reported that a feeder layer consisting of mitotically inactivated MEFs or other fibroblasts is required for human ES cells to remain in an undifferentiated state (see e.g., U.S. Pat. No. 6,200,806; Amit et al., Developmental Biology 227:271-78, 2000; Odorico et al., Stem Cells 19:193-204, 2001). However, while mouse ES cells will also remain undifferentiated in the absence of an embryonic fibroblast feeder layer so long as the medium is supplemented with LIF (Smith et al., Nature 336:688-690, 1988; Williams et al., Nature 336:684-687, 1988), human ES cells differentiate or die in the absence of a fibroblast feeder layer, even when the medium is supplemented with LIF (Thomson et al., 1998 supra; Reubinoff et al., 2000 supra).

The exact role of the MEFs in establishment and maintenance of a ES cell culture is not known. Possible roles for the MEFs include prevention of differentiation or death, or induction of proliferation, by one or some of a number of mechanisms, including, but not limited to the production of cytokines such as LIF, the provision of extracellular matrix components that provide attachment sites for the ES cells, the provision of receptor-style interactions that provide survival signals for the ES cells, the presentation of cytokines to the ES cells, the adsorption of environmental toxins such as heavy metals, or the secretion of growth factors necessary to support the ES cell.

While fibroblast feeder layers are critical to the survival and non-differentiation of the human ES cell, mouse embryonic fibroblast feeder cells are labor-intensive to derive, and can vary between lots (Amit et al., supra, 2000). The development and use of non-fibroblast feeder cell layers that are not labor-intensive to establish, and that offer greater consistency than embryonic fibroblast cells would be an advantage to the field. Moreover, the potential applications for the human ES cell are limited when the ES cell is cultured in the presence of non-human feeder cell layers. Ideally, a human ES cell could be cultured with human feeder cell layers, or could be cultured in the presence medium conditioned by human cells.

There is no evidence in the prior art showing the long-term isolation and/or maintenance of human pluripotent ES cells on non-fibroblast feeder cells. Others have attempted to isolate human ES cells on non-fibroblast feeder cells, but have not succeeded in maintaining the human ES cells in a pluripotent state for long or indefinite periods of time. Bongso et al. cultured human blastocysts on oviduct epithelial cells in the presence of human LIF (Bongso et al., Human Reproduction 9:2100-2117, 1994). Bongso et al. then separated the ICMs from the trophoblast and feeder cells, and replated the ICM-derived cells in the absence of a feeder layer. This method supported the growth of ICM-derived cells for two subcultures, or at least 18 days, without differentiation; however, the cells subsequently differentiated into fibroblasts or died.

Similarly, there is no evidence in the prior art showing the long-term isolation and or maintenance of human pluripotent ES cells in the presence of conditioned media from human cell types. Although the co-culture of human ES cells with conditioned media from mouse embryonic fibroblasts has been reported (Xu et al., Keystone Symposia Abstract Book, Pluripotent Stem Cells: Biology and Applications, February 2001, A. 133), conditioned medium from human cell cultures has not been reported to maintain human ES cells in a pluripotent state.

Granulosa cells are the cells that support and nourish the oocyte in the ovary. Granulosa cells are thought to arise from a population of stem cells (Rodgers et al., Mol Cell Endocrinol 22;171(1-2):41-8, 2001; Lavranos et al., Biology of Reproduction 61, 358-366, 1999; Rodgers et al., J Reprod Fertil Suppl 54:343-52, 1999). Initially, a primordial follicle consists of an oocyte surrounded by a single layer of flattened epithelial pregranulosa cells. As the follicle grows, the granulosa cells proliferate radially, reaching a total of tens of thousands of cells in the preovulatory state. Granulosa cells cease dividing at ovulation, and after ovulation, granulosa cells differentiate into the luteal cells of the developing corpus luteum in the ovary. See also generally, Weiss, et al., Eur J Endocrinol. 144(6):677-85, June 2001; Stevenson, Indian J Exp Biol. 2000 December;38(12):1183-91; Hosokawa et al., Endocrinol; 138(11):4679-4687, 1998; Hosokawa et al., Endocrinology 138(11):4688-4700, 1998; Byong-Lyul et al., Mol and Cell. Endocrinology 120:169-176, 1996.

Researchers have attempted to use pig granulosa cells as feeder cell to support the isolation and/or maintenance of pig and cow ES cells (Vasil'eva and Vasil'ev, 1995 Russian J. Dev. Biol., 26:167-72, Translated from Ontogenez, 26:206-12, 1995; Vasil'ev and Vasil'eva, 1995 Russian J. Dev. Biol., 26:163-66, Translated from Ontogenez, 26:201-205, 1995). Pig embryos did not attach to pig granulosa cells, and while pig embryonic cells did attach to pig granulosa cells, the cultured embryonic cells produced trophoblast-like cells and not ES-like cells (Vasil'ev and Vasil'eva, 1995 supra). Cow embryos did attach to pig granulosa cells, and formed ES-like cells that could be maintained in culture on granulosa cell feeder layers for three transfers without differentiating (Vasil'eva and Vasil'ev, 1995 supra). Thus the culture conditions which were successful with one large domestic animal were not successful for another domestic animal. The authors acknowledge that the techniques useful for the isolation of ES cells from large domestic animals will differ from those useful for the isolation of ES cells from mice. It is therefore not predictable that a technique successful for the isolation and short-term maintenance of ES-like cells from cows will be useful for the isolation and/or maintenance of human pluripotent stem cells.

For the treatment of many human diseases by cell therapy, it may be necessary to direct the differentiation of human ES cells in culture, prior to transplanting the ES cells into the subject. In vitro differentiation may be directed by the addition of supplemental growth factors to the culture medium.

Various soluble factors have been used to induce differentiation of mouse ES cells down specific lineages: IL-3 directs cells to become macrophages, mast cells or neutrophils (Wiles, M. V., and Keller, G., Development 111:259-267, 1991); IL-6 directs cells to the erythroid lineage (Biesecker, L. G. and Emerson, S. G., Exp. Hematol., 21:774-778, 1993); retinoic acid induces neuron formation (Slager et al., Dev. Genet. 14:212-224, 1993; Bain et al., Dev. Biol. 168:342-357, 1995); and transforming growth factor (TGF)-$\beta$1 induces myogenesis (Slager et al., supra, 1993; Rohwedel et al., Dev. Biol. 164:87-101, 1994). Most of these studies were performed on ES cells that had been induced to form embryoid bodies in culture (Slager et al., supra, 1993; Bain et al., Supra, 1995; Rohwedel et al., supra, 1994). While the use of the soluble factors induced differentiation of different cell lineages, the factors did not induce differentiation of only one cell type; instead, the factors changed the proportion of the different cell types in the cultures.

The most comprehensive analysis of human ES cells examined the effects of eight growth factors on the differentiation of cells grown first as embryoid bodies and then disaggregated (Schuldiner et al., 2000; PNAS USA 97:11307-11312). Schuldiner et al. applied basic fibroblast growth factor (bFGF), TGF-$\beta$1, activin-A, bone morphogenetic protein 4 (BMP-4), hepatocyte growth factor (HGF), epidermal growth factor (EGF), $\beta$ nerve growth factor ($\beta$NGF), and retinoic acid to the cells, and determined the effects on cell-specific gene expression and cell morphology. TGF-$\beta$1 and activin-A induced differentiation of muscle cells; retinoic acid, bFGF, BMP-4, and EGF induced differentiation of ectodermal and mesodermal cells; while NGF and HGF allowed differentiation of cells from all three germ layer lineages. However, none of the growth factors tested directed the differentiation of a uniform and singular cell type.

Finally, Reubinoff et al. were able to isolate human neuronal-lineage cells in a relatively pure form from a human ES culture (Reubinoff et al., 2000 supra). The differentiation of neuronal-lineage cells occurred spontaneously when the human ES cell was cultured on mouse embryonic fibroblasts. Reubinoff et al. isolated the areas of differentiated cells and re-plated the cells in serum free medium. The cells formed spheres, which were again re-plated and allowed to attach to an adhesive substrate. Although this procedure provided a relatively pure population, these cells cannot be used for the treatment of humans since they were cultured on mouse feeder cells. Additionally, the differentiation was not directed towards a specific lineage. There is a need, therefore, to develop methods for the directed differentiation of human ES cells that are not cultured with mouse feeder cells. These methods may involve the addition of a supplemental growth factor to the culture medium.

There is a need, therefore, to establish culture conditions, such as human feeder cells, or conditioned medium, that allow for greater reproducibility and consistency among cultures, and that allow for the use of the human ES cells in cell therapies. There is also a need to establish methods for selectively differentiating human ES cells into precursors and into the desired and uniform cell lineages, such as the neuronal cell lineage. Large, purified populations of selectively differentiated ES cells will provide a potentially limitless source of cells for cellular therapy treatments and further drug discovery. Selectively differentiated, and reversibly differentiated, ES cells can be used for cell therapy, and transplanted into subjects to treat a number of different conditions and diseases.

SUMMARY OF THE INVENTION

The invention provides for the isolation and/or maintenance of human pluripotent ES cells. The present invention provides a human pluripotent ES cell culture that includes a human ES cell and a human feeder cell. In a preferred embodiment, the human feeder cell is selected from the group consisting of a human fibroblast cell, a MRC-5 cell, a human embryonic kidney cell, a mesenchymal cell, an osteosarcoma cell, a keratinocyte, a chondrocyte, a Fallopian ductal epithelial cell, a liver cell, a cardiac cell, a bone marrow stromal cell, a granulosa cell, a skeletal muscle cell, and an aortic endothelial cell. In a more preferred embodiment the human feeder cell is selected from the group consisting of a skin keloid fibroblast cell, a fetal skin fibroblast cell, a bone marrow stromal cell, or a skeletal muscle cell. The invention further provides methods for the isolation and maintenance of a human pluripotent ES cell in the presence of a human feeder cell.

The invention provides a human pluripotent ES cell culture that includes the human pluripotent ES cell and a conditioned medium. The invention further provides the conditioned medium maintains the human pluripotent ES cell in a pluripotent state. In a preferred embodiment the conditioned medium is obtained from the human feeder cell.

The invention further provides for a human pluripotent ES cell culture comprising the human pluripotent ES cell and a human feeder cell factor conditioned medium.

The invention provides for a human pluripotent ES cell cultured in the presence of a supplemental growth factor. The invention provides that the supplemental growth factor is selected from the group consisting of SCF, OSM, CNTF, IL-6 in combination with soluble IL-6R, FGF, BMP, TNF, and GM-CSF. In a preferred embodiment, a supplemental growth factor is added to the conditioned medium obtained from the human feeder cell.

The invention provides a method of maintaining a human pluripotent ES cell culture, comprising culturing selected ES colonies on a human feeder cell layer. In a preferred embodiment, the feeder cell is selected from the group consisting of a human fibroblast cell, a MRC-5 cell, a human embryonic kidney cell, a mesenchymal cell, an osteosarcoma cell, a keratinocyte, a chondrocyte, a Fallopian ductal epithelial cell, a liver cell, a cardiac cell, a bone marrow stromal cell, a granulosa cell, a skeletal muscle cell, a muscle cell and an aortic endothelial cell. In a more preferred embodiment, the human feeder cell is selected from the group consisting of a skin keloid fibroblast cell, a fetal skin fibroblast cell, a bone marrow stromal cell, a Fallopian ductal epithelial cell, or a skeletal muscle cell. In a preferred embodiment, the feeder cell expresses leukemia inhibitory factor, steel cell factor, and FGF.

The invention further provides a method of maintaining a human pluripotent ES cell culture comprising the steps of: (a) isolating cells from the inner cell mass of a blastocyst; (b) plating the inner cell mass cells, wherein inner cell mass-derived cell masses are formed; and (c) re-plating and maintaining the cell masses on a human feeder cell layer to thereby maintain a human pluripotent ES cell.

The invention further provides a method of isolating and maintaining a human pluripotent ES cell culture, comprising the steps of: (a) isolating cells from the inner cell mass of a blastocyst; (b) plating the inner cell mass cells on a human feeder cell layer, wherein inner cell mass-derived cell masses are formed; (c) dissociating the mass into dissociated cells; (d) re-plating the dissociated cells on a human feeder cell layer; (e) selecting colonies with the characteristics of human ES cells; (f) re-plating and maintaining the colonies on a human feeder cell layer to thereby maintain a human pluripotent ES cell.

The present invention provides a method for isolating and maintaining a human pluripotent ES cell, further comprising culturing the human pluripotent ES cell in the presence of conditioned medium. The invention provides that the conditioned medium is obtained from a human cell. In a more embodiment, the human cell is selected from the group consisting of a skin keloid fibroblast cell, a fetal skin fibroblast cell, a bone marrow stromal cell, a Fallopian ductal epithelial cell or a skeletal muscle cell. The conditioned medium may further comprise a supplemental growth factor.

The invention further provides for the isolation and use of a human feeder cell factor. The cell factor can be isolated from a human feeder cell, or the conditioned medium obtained from a human feeder cell.

The present invention provides a method of isolating and maintaining a human pluripotent ES cell comprising the steps of: (a) isolating cells from the inner cell mass of a blastocyst; (b) plating the inner cell mass cells on a human feeder cell layer, wherein inner cell mass-derived cell masses are formed; (c) dissociating the mass into dissociated cells; (d) re-plating the dissociated cells on a human feeder cell layer; (e) selecting colonies with the characteristics of human ES cells; and (f) re-plating and maintaining the colonies in a human conditioned medium to thereby maintain a human pluripotent ES cell.

In another embodiment, the invention provides for maintaining the human pluripotent ES cell that was re-plated in a human feeder cell conditioned medium further in the presence of a supplemental growth factor, wherein the supplemental growth factor is selected from one or more of the group consisting of SCF, OSM, CNTF, IL-6 in combination with soluble IL-6R, FGF, BMP, TNF, and GM-CSF.

The invention further provides culture additions, such as feeder cells or conditioned medium, for the selective differentiation of human ES cells, and for the selectively reversible differentiation of human ES cells.

The invention further provides for a human pluripotent ES cell generated by any of the methods described herein. The invention additionally provides for a tissue generated by any of the human pluripotent ES cells described herein. The invention further provides that the cell and tissues generated using the invention can be used in cell therapy to experimentally, therapeutically or prophylactically treat a disease or condition in a human or animal. Preferably the disease is selected from the group consisting of Parkinson's, Alzheimer's, Multiple Sclerosis, spinal cord injuries, stroke, macular degeneration, burns, liver failure, heart disease, diabetes, Duchenne's muscular dystrophy, osteogenesis imperfecta, osteoarthritis, rheumatoid arthritis, anemia, leukemia, breast cancer, solid tumors, and AIDS. In preferred embodiments, the disease is Parkinson's or Alzheimer's.

DETAILED DESCRIPTION OF THE INVENTION

Figure 1:
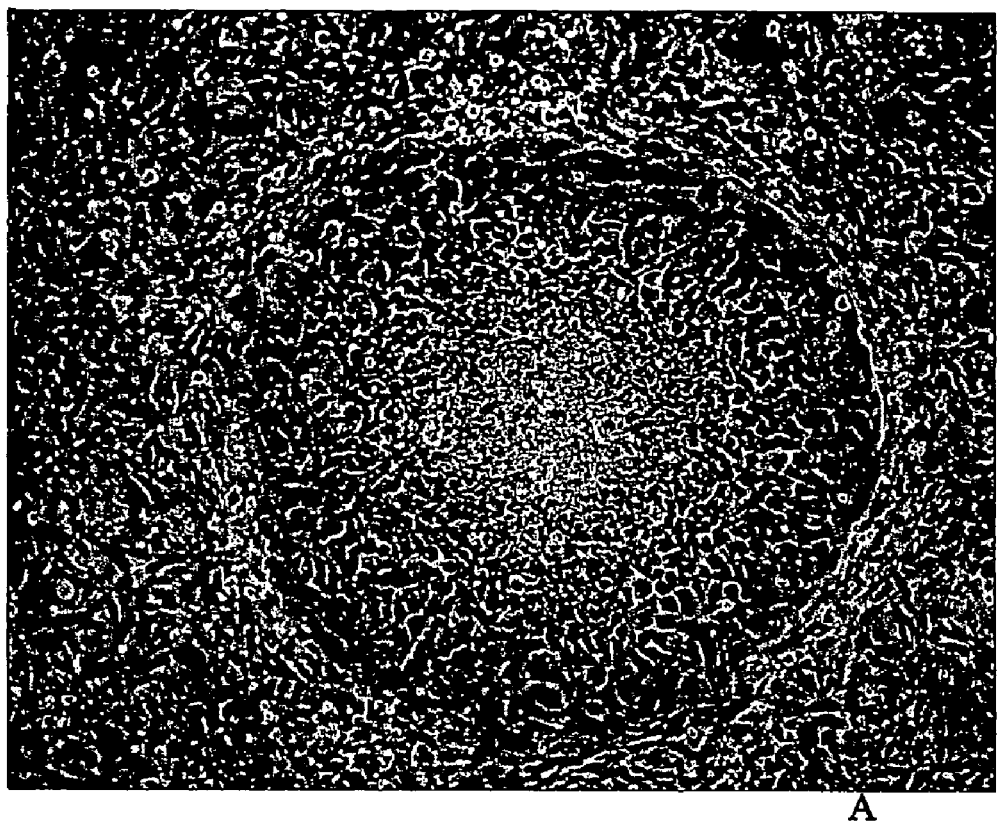
FIGS. 1A and 1B show unstained phase-contrast images of BGN01 human embryonic stem cells grown on HS-5 feeder cells for 1 day (A) and 6 days (B) respectively. Note the initial thinning of the cell layer, followed by a thickening at the periphery of the colony. These peripheral cells had the morphology of pluripotent stem cells, and were used for passaging and their expression of markers of pluripotent cells was confirmed by immunostaining.
Figure 1:
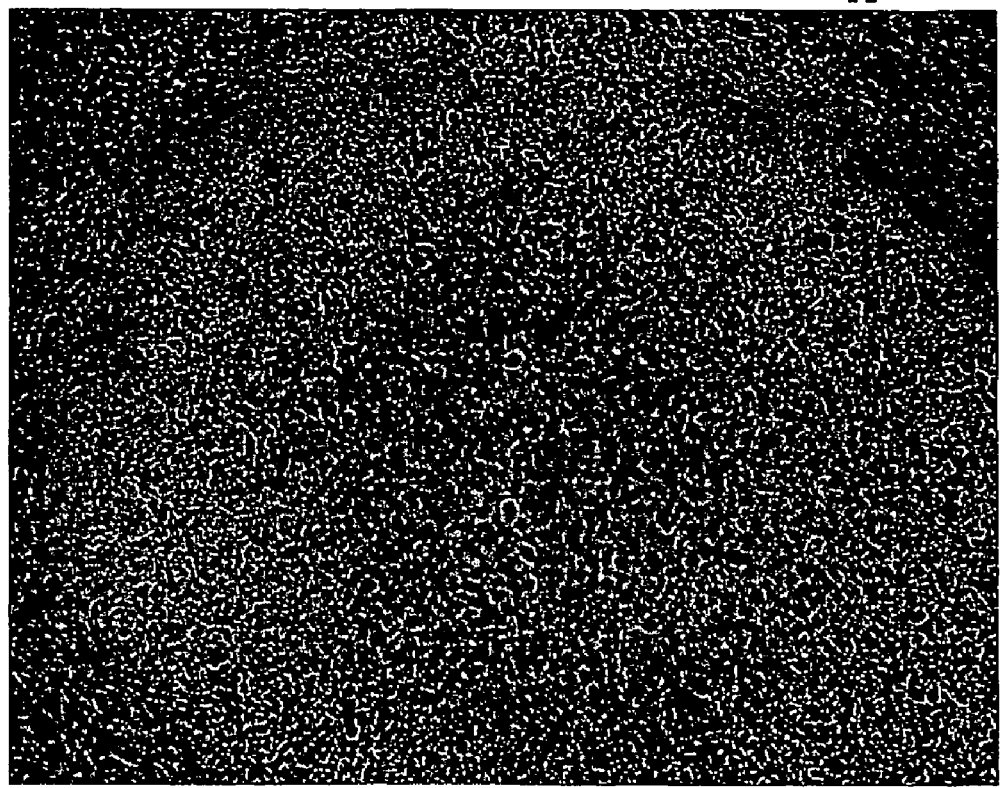
Figure 2:
FIGS. 2A-J show immunostaining of BGN01 cells grown on HS-5 cells for 15 days at the time of staining. The cells stain positively for OCT-4 (FIG. 2A), Tra-1-60 (FIG. 2C), SSEA-3 (FIG. 2E), and SSEA-4, (FIG. 2H). The cells are negative for SSEA1 (FIG. 2J). For each marker, the same cells were counterstained with the nuclear stain, DAPI (FIGS. 4B, D, F, H, and J). Note that the colonies express all the epitopes, except SSEA1, and that the feeder cells, which can be visualized after DAPI staining, are not immunoreactive with any of the antibodies.
Figure 2:
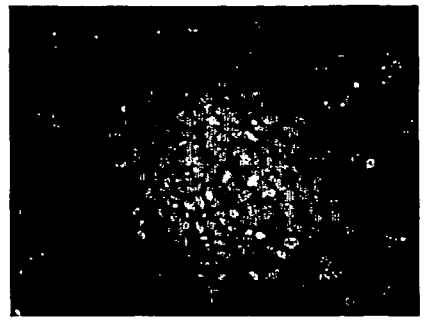
Figure 2:
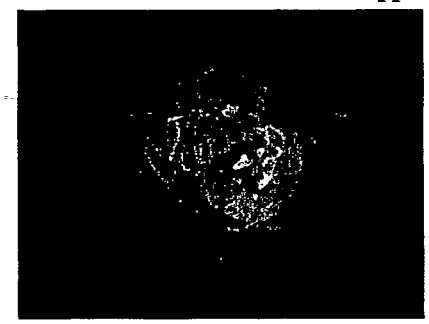
Figure 2:
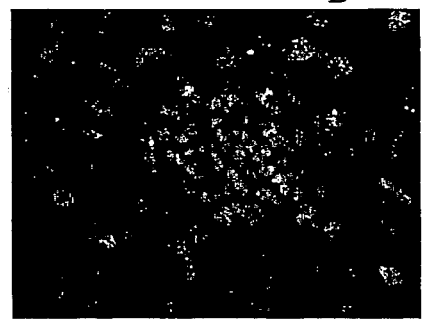
Figure 2:
Figure 2:
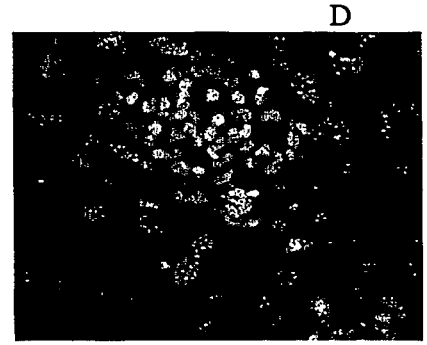
Figure 2:
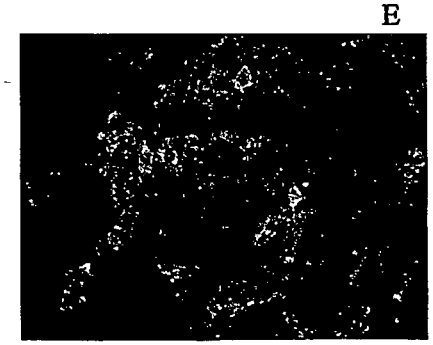
Figure 2:
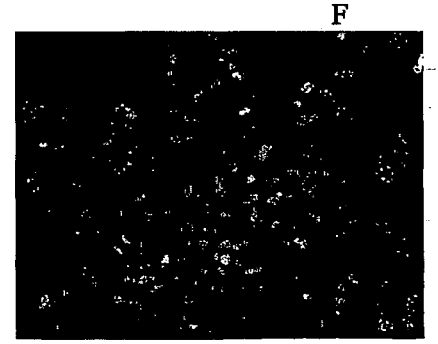
Figure 2:
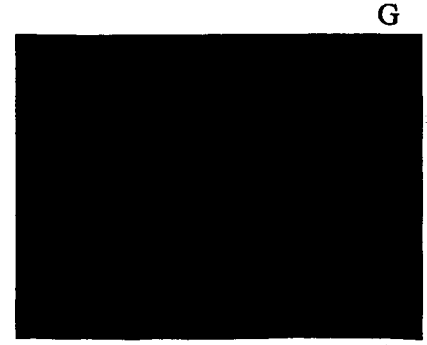
Figure 2:
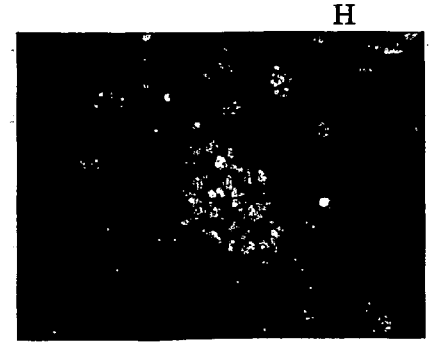

The present invention may be understood more readily by reference to the following detailed description of the preferred embodiments of the invention and the Examples included herein. However, before the present compounds, compositions, and methods are disclosed and described, it is to be understood that this invention is not limited to specific cell types, specific feeder cell layers, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting.

It must be noted that as used herein and in the appended claims, the singular forms "a," "an," and "the," include plural referents unless the context clearly indicates otherwise. Thus, for example, reference to "a cell" includes one or more of such different cells, and reference to "the method" includes reference to equivalent steps and methods known to those of ordinary skill in the art that could be modified or substituted for the methods described herein.

Unless otherwise defined, all technical and scientific terms used herein have the meaning as commonly understood by one of ordinary skill in the art to which this invention belongs. The practice of the present invention employs, unless otherwise indicated, conventional techniques of cell biology, molecular biology, genetics, chemistry, microbiology, recombinant DNA, and immunology. See, e.g., Maniatis et al. (1982) Molecular Cloning, A Laboratory Manual, latest edition, Cold Spring Harbor Laboratory, Cold Spring Harbor, N.Y.; Sambrook et al. (1989) Molecular Cloning: A Laboratory Manual, latest edition (Cold Spring Harbor, N.Y.: Cold Spring Harbor Laboratory Press); Ausubel et al. (1992) Current Protocols in Molecular Biology, latest edition (New York: John Wiley & Sons); Guthrie & Fink (1991) Methods Enzymol. 194:1-863; Cell Biology, A Laboratory Manual, ed. Celis, J. E., Academic Press, NY; Histochemistry, Pearse, A. G. E., Vol. 1 (1980), Vol. 2 (1985), and Vol. 3 (1990).

The invention encompasses a human pluripotent stem cell culture, comprising a human pluripotent stem cell and a human feeder cell. In a preferred embodiment, the human pluripotent stem cell is an embryonic stem cell. In one embodiment, the human feeder cell is selected from the group consisting of a human fibroblast cell, a MRC-5 cell, a human embryonic kidney cell, a mesenchymal cell, an osteosarcoma cell, a keratinocyte, a chondrocyte, a Fallopian ductal epithelial cell, a liver cell, a cardiac cell, a bone marrow stromal cell, a granulosa cell, a skeletal muscle cell, a muscle cell and an aortic endothelial cell. In a preferred embodiment, the MRC-5 cell, a diploid lung cell line, has ATCC Catalog Number 55-X; the human embryonic kidney cell has ATCC Accession Number CRL-1573.1; the human keratinocyte is retrovirally transformed and has ATCC Accession Number CRL-2309; the human osteosarcoma cell has ATCC Accession Number HTB-96; and the mesenchymal cell is a human fetal palatal mesenchymal cell with ATCC Accession Number CRL-1486. In other preferred embodiments the human fibroblast cell is a skin keloid fibroblast, KEL FIB and has ATCC Accession Number CRL-1762, or is a fetal skin fibroblast cell; and the bone marrow stromal cell, HS-5, has ATCC Accession Number CRL-11882. In a preferred embodiment, the human feeder cell is a cell line, wherein the cell line is selected from the group consisting of a human fibroblast cell, a MRC-5 cell, a human embryonic kidney cell, a mesenchymal cell, an osteosarcoma cell, a keratinocyte, a chondrocyte, a Fallopian ductal epithelial cell, and a liver cell. In another embodiment, the human feeder cell is a primary cell, wherein the primary cell is selected from the group consisting of a cardiac cell, a mesenchymal cell, an aortic endothelial cell, a keratinocyte, a bone marrow stromal cell, a chondrocyte, a granulosa cell, a Fallopian ductal epithelial cell, an osteosarcoma cell, a fibroblast cell, a muscle cell and a liver cell. In another preferred embodiment, the human feeder cell is a skeletal muscle cell. In another embodiment the human feeder cell layer has the characteristics of a bone marrow stromal cell, a granulosa cell, a skin keloid fibroblast cell, a fetal skin fibroblast cell, a Fallopian ductal epithelial cell and a skeletal muscle cell. Further, the invention contemplates that the human feeder cell of the preceding embodiments can be a mitotically inactivated human feeder cell.

The invention also encompasses a human pluripotent stem cell culture comprising a human pluripotent stem cell and a human feeder cell conditioned medium. In a preferred embodiment, the human pluripotent stem cell is an embryonic stem cell. In one embodiment, the human feeder cell is selected from the group consisting of a human fibroblast cell, a MRC-5 cell, a human embryonic kidney cell, a mesenchymal cell, an osteosarcoma cell, a keratinocyte, a chondrocyte, a Fallopian ductal epithelial cell, a liver cell, a cardiac cell, a bone marrow stromal cell, a muscle cell, a granulosa cell, a skeletal muscle cell, and an aortic endothelial cell. In a preferred embodiment, the human feeder cell is a cell line, wherein the cell line is selected from the group consisting of a human fibroblast cell, a MRC-5 cell, a human embryonic kidney cell, a mesenchymal cell, an osteosarcoma cell, a keratinocyte, a chondrocyte, a Fallopian ductal epithelial cell, and a liver cell. In a preferred embodiment the cell line is selected from the group consisting of a fibroblast cell, where the human fibroblast cell is a skin keloid fibroblast, KEL FIB having ATCC Accession Number CRL-1762 or is a fetal skin fibroblast cell; a skeletal muscle cell; and a bone marrow stromal cell where the bone marrow stromal cell, HS-5, has ATCC Accession Number CRL-11882. Alternatively the bone marrow stromal cell is HS-27 (ATCC Accession Number CRL-2496). In another embodiment, the human feeder cell is a primary cell, wherein the primary cell is selected from the group consisting of a cardiac cell, a mesenchymal cell, a keratinocyte, a bone marrow stromal cell, a muscle cell, a chondrocyte, a granulosa cell, an aortic endothelial cell, a Fallopian ductal epithelial cell, an osteosarcoma cell, and a liver cell. In a preferred embodiment, the human feeder cell is a skeletal muscle cell, a fetal skin fibroblast cell, or a Fallopian ductal epithelial cell. The human feeder cell can be a mitotically inactivated cell. In a preferred embodiment, the feeder cell expresses leukemia inhibitory factor, steel cell factor, and FGF.

The human pluripotent stem cell culture of the above embodiments can further comprise one or more supplemental growth factors. In one embodiment, one or more supplemental growth factors are selected from the group consisting of SCF, OSM, CNTF, IL-6 in combination with soluble IL-6R, FGF, BMP, TNF, and GM-CSF.

The invention encompasses a human pluripotent stem cell culture comprising the human pluripotent stem cell and a human feeder cell factor conditioned medium. In a preferred embodiment, the human pluripotent stem cell is an embryonic stem cell.

The invention further encompasses a tissue generated from any of the cell cultures of the aforementioned embodiments.

The invention encompasses a method of maintaining a human pluripotent stem cell culture, comprising culturing a human stem cell on a human feeder cell layer. In a preferred embodiment, the human stem cell is an embryonic stem cell. In a further embodiment, the human stem cell is a selected stem cell. In yet another embodiment, embodiment, the human stem cell is a selected embryonic stem cell. In a preferred embodiment, the human feeder cell layer is selected from the group consisting of a human fibroblast cell, a MRC-5 cell, a human embryonic kidney cell, a mesenchymal cell, an osteosarcoma cell, a keratinocyte, a chondrocyte, a Fallopian ductal epithelial cell, a muscle cell, a liver cell, a cardiac cell, a bone marrow stromal cell, a granulosa cell, a skeletal muscle cell, and an aortic endothelial cell. In a preferred embodiment, the human feeder cell is a cell line, wherein the cell line is selected from the group consisting of a human fibroblast cell, a MRC-5 cell, a human embryonic kidney cell, a mesenchymal cell, an osteosarcoma cell, a keratinocyte, a chondrocyte, a Fallopian ductal epithelial cell, and a liver cell. In preferred embodiments the human fibroblast cell is a skin keloid fibroblast, KEL FIB and has ATCC Accession Number CRL-1762 or is a fetal skin fibroblast cell; and the bone marrow stromal cell, HS-5, has ATCC Accession Number CRL-11882. In another embodiment, the human feeder cell is a primary cell, wherein the primary cell is selected from the group consisting of a cardiac cell, a mesenchymal cell, a keratinocyte, a bone marrow stromal cell, a chondrocyte, a granulosa cell, a Fallopian ductal epithelial cell, an osteosarcoma cell, and a liver cell. In another preferred embodiment, the human feeder cell is a skeletal muscle cell, a Fallopian ductal epithelial cell or a granulosa cell.

The invention further encompasses a method of maintaining a human pluripotent embryonic stem cell culture, comprising culturing selected embryonic stem cell colonies with a human feeder cell. In a preferred embodiment, the human feeder cell is selected from the group consisting of a human fibroblast cell, a MRC-5 cell, a human embryonic kidney cell, a mesenchymal cell, an osteosarcoma cell, a keratinocyte, a chondrocyte, a Fallopian ductal epithelial cell, a liver cell, a cardiac cell, a bone marrow stromal cell, a granulosa cell, a skeletal muscle cell, and an aortic endothelial cell. In the most preferred embodiment the human feeder cell is selected from the group consisting of a skin keloid fibroblast, a fetal skin fibroblast cell, a granulosa cell, a skeletal muscle cell, a Fallopian ductal epithelial cell and a bone marrow stromal cell. In one embodiment the skin keloid fibroblast is KEL FIB and has ATCC Accession Number CRL-1762; and the bone marrow stromal cell, HS-5, has ATCC Accession Number CRL-11882. Alternatively the bone marrow stromal cell is HS-27 (ATCC Accession Number CRL-2496).

The invention encompasses a method of maintaining a human pluripotent embryonic stem cell culture, comprising the steps of: (a) isolating cells from the inner cell mass of a blastocyst; (b) plating the inner cell mass cells, wherein inner cell mass-derived cell masses are formed; (c) selecting colonies with the characteristics of human embryonic stem cells; and (d) re-plating and maintaining the colonies on a human feeder cell layer to thereby maintain a human pluripotent embryonic stem cell. In one embodiment, the inner cell mass-derived cells are dissociated, and re-plated on a mouse embryonic fibroblast cell. In a preferred embodiment, the human feeder cell layer is selected from the group consisting of a human fibroblast cell, a MRC-5 cell, a human embryonic kidney cell, a mesenchymal cell, an osteosarcoma cell, a keratinocyte, a chondrocyte, a Fallopian ductal epithelial cell, a liver cell, a cardiac cell, a bone marrow stromal cell, a granulosa cell, a skeletal muscle cell, and an aortic endothelial cell. In the most preferred embodiment the human feeder cell is selected from the group consisting of a skin keloid fibroblast, a fetal skin fibroblast cell, a granulosa cell, a skeletal muscle cell, a Fallopian ductal epithelial cell and a bone marrow stromal cell.

The invention further encompasses a method of maintaining a human pluripotent embryonic stem cell culture, comprising the steps of: (a) isolating cells from the inner cell mass of a blastocyst; (b) plating the inner cell mass cells, wherein inner cell mass-derived cell masses are formed; and (c) re-plating and maintaining a human embryonic stem cell colony on a human feeder cell layer to thereby maintain a human pluripotent embryonic stem cell. In this method, the human feeder cell layer is selected from the group consisting of a human fibroblast cell, a MRC-5 cell, a human embryonic kidney cell, a mesenchymal cell, an osteosarcoma cell, a keratinocyte, a chondrocyte, a Fallopian ductal epithelial cell, a liver cell, a cardiac cell, a bone marrow stromal cell, a granulosa cell, a skeletal muscle cell, and an aortic endothelial cell. In a preferred embodiment the human fibroblast cell is a skin keloid fibroblast, KEL FIB having ATCC Accession Number CRL-1762 or a fetal skin fibroblast cell; and the bone marrow stromal cell, HS-5, has ATCC Accession Number CRL-11882.

In another embodiment the invention encompasses a method of isolating and maintaining a human pluripotent embryonic stem cell culture, comprising the steps of: (a) isolating cells from the inner cell mass of a blastocyst; (b) plating the inner cell mass cells on a human feeder cell, wherein inner cell mass-derived cell masses are formed; (c) dissociating the inner cell mass-derived cell masses into dissociated cells; (d) re-plating the dissociated cells on a human feeder cell; (e) selecting colonies with the characteristics of human embryonic stem cells; and (f) re-plating and maintaining the colonies on a human feeder cell to thereby isolate and maintain a human pluripotent embryonic stem cell. The human feeder cell is selected from the group consisting of a human fibroblast cell, a MRC-5 cell, a human embryonic kidney cell, a mesenchymal cell, an osteosarcoma cell, a keratinocyte, a chondrocyte, a Fallopian ductal epithelial cell, a liver cell, a muscle cell, a cardiac cell, a bone marrow stromal cell, a granulosa cell, a skeletal muscle cell, and an aortic endothelial cell. In a preferred embodiments the human fibroblast cell is a skin keloid fibroblast, KEL FIB having ATCC Accession Number CRL-1762; and the bone marrow stromal cell, HS-5, has ATCC Accession Number CRL-11882. Alternatively the bone marrow stromal cell is HS-27 (ATCC Accession Number CRL-2496).

The invention further encompasses a method of isolating and maintaining a human pluripotent embryonic stem cell culture, comprising the steps of: (a) isolating cells from the inner cell mass of a blastocyst; (b) plating the inner cell mass cells on a human feeder cell, wherein inner cell mass-derived cell masses are formed; and (c) re-plating the inner cell mass-derived cell mass, and maintaining a human embryonic stem cell colony on a human feeder cell to thereby isolate and maintain a human pluripotent embryonic stem cell. The human feeder cell is selected from the group consisting of a human fibroblast cell, a MRC-5 cell, a human embryonic kidney cell, a mesenchymal cell, an osteosarcoma cell, a keratinocyte, a chondrocyte, a Fallopian ductal epithelial cell, a liver cell, a cardiac cell, a bone marrow stromal cell, a granulosa cell, a skeletal muscle cell, and an aortic endothelial cell. In a preferred embodiments the human fibroblast cell is a skin keloid fibroblast, KEL FIB and has ATCC Accession Number CRL-1762 or a fetal skin fibroblast cell; and the bone marrow stromal cell, HS-5, has ATCC Accession Number CRL-11882. Alternatively the bone marrow stromal cell is HS-27 (ATCC Accession Number CRL-2496).

The invention includes a method of maintaining a human pluripotent embryonic stem cell culture, comprising culturing a selected embryonic stem cell colony in a human feeder cell factor conditioned medium. In a preferred embodiment, the human feeder cell is selected from the group consisting of a human fibroblast cell a MRC-5 cell, a human embryonic kidney cell, a mesenchymal cell, an osteosarcoma cell, a keratinocyte, a chondrocyte, a Fallopian ductal epithelial cell, a liver cell, a muscle cell, a cardiac cell, a bone marrow stromal cell, a granulosa cell, a skeletal muscle cell, and an aortic endothelial cell. In the most preferred embodiment the human feeder cell is selected from the group consisting of a skin keloid fibroblast, a fetal skin fibroblast cell, a granulosa cell, a skeletal muscle cell, a Fallopian ductal epithelial cell and a bone marrow stromal cell. In a preferred embodiment the skin keloid fibroblast, KEL FIB has ATCC Accession Number CRL-1762, and the bone marrow stromal cell, HS-5, has ATCC Accession Number CRL-11882.

The invention further encompasses a method of maintaining a human pluripotent embryonic stem cell culture, comprising the steps of:(a) isolating cells from the inner cell mass of a blastocyst; (b) plating the inner cell mass cells on a mouse embryonic fibroblast cell, wherein inner cell mass-derived cell masses are formed; (c) dissociating the inner cell mass-derived cell masses into dissociated cells; (d) re-plating the dissociated cells on a mouse embryonic fibroblast cell; (e) selecting colonies with the characteristics of human ES cells; (f) re-plating the colonies in the absence of a feeder cell; and (g) adding a human feeder cell conditioned medium to thereby maintain a human pluripotent embryonic stem cell. In a preferred embodiment, the human feeder cell conditioned medium is obtained from a cell selected from the group consisting of a human fibroblast cell, a MRC-5 cell, a human embryonic kidney cell, a mesenchymal cell, an osteosarcoma cell, a keratinocyte, a chondrocyte, a Fallopian ductal epithelial cell, a liver cell, a muscle cell, a cardiac cell, a bone marrow stromal cell, a granulosa cell, a skeletal muscle cell, and an aortic endothelial cell. In the most preferred embodiment the human feeder cell is selected from the group consisting of a skin keloid fibroblast, a fetal skin fibroblast cell, a granulosa cell, a skeletal muscle cell, a Fallopian ductal epithelial cell and a bone marrow stromal cell. In a preferred embodiment the skin keloid fibroblast, KEL FIB, has ATCC Accession Number CRL-1762; and the bone marrow stromal cell, HS-5, has ATCC Accession Number CRL-11882. Alternatively the bone marrow stromal cell is HS-27 (ATCC Accession Number CRL-2496).

In another embodiment, the invention encompasses a method of isolating and maintaining a human pluripotent embryonic stem cell culture, comprising the steps of: (a) isolating cells from the inner cell mass of a blastocyst; (b) plating the inner cell mass cells on a human feeder cell, wherein inner cell mass-derived cell masses are formed; (c) dissociating the inner cell mass-derived cell masses into dissociated cells; (d) re-plating the dissociated cells on a human feeder cell; (e) selecting colonies with the characteristics of human ES cells; (f) re-plating the colonies in the absence of a feeder cell; and (g) adding a human feeder cell conditioned medium to thereby isolate and maintain a human pluripotent embryonic stem cell. In a preferred embodiment, the human feeder cell conditioned medium is obtained from a cell selected from the group consisting of a human fibroblast cell, a MRC-5 cell, a human embryonic kidney cell, a mesenchymal cell, an osteosarcoma cell, a keratinocyte, a chondrocyte, a Fallopian ductal epithelial cell, a liver cell, a muscle cell, a cardiac cell, a bone marrow stromal cell, a granulosa cell, a skeletal muscle cell, and an aortic endothelial cell. In the most preferred embodiment the human feeder cell is selected from the group consisting of a skin keloid fibroblast, a fetal skin fibroblast cell, a granulosa cell, a skeletal muscle cell, a Fallopian ductal epithelial cell and a bone marrow stromal cell. In a preferred embodiment the skin keloid fibroblast, KEL FIB, has ATCC Accession Number CRL-1762; and the bone marrow stromal cell, HS-5, has ATCC Accession Number CRL-11882.

The invention encompasses a further embodiment, whereby the aforementioned methods further comprise one or more supplemental growth factors. In one embodiment, one or more supplemental growth factors are selected from the group consisting of SCF, OSM, CNTF, IL-6 in combination with soluble IL-6R, FGF, BMP, TNF, and GM-CSF. In a preferred embodiment, the feeder cell expresses leukemia inhibitory factor, steel cell factor, and FGF.

The invention encompasses a human pluripotent embryonic stem cell cultured by any of the aforementioned methods. The invention further encompasses a tissue generated from the cell culture of any of the aforementioned methods.

In another embodiment, the invention encompasses a method of using the cell or tissue of any of the aforementioned embodiments for the experimental, therapeutic and prophylactic treatment of a disease or condition in a human or animal. Preferably, the disease is selected from the group consisting of Parkinson's, Alzheimer's, Multiple Sclerosis, spinal cord injuries, stroke, macular degeneration, burns, liver failure, heart disease, diabetes, Duchenne's muscular dystrophy, osteogenesis imperfecta, osteoarthritis, rheumatoid arthritis, anemia, leukemia, breast cancer, solid tumors, and AIDS. In a preferred embodiment, the disease is Parkinson's or Alzheimer's. In a more preferred embodiment, the disease is Parkinson's.

The term "human pluripotent stem cell" encompasses stem cells obtained from human embryos, fetuses or adult tissues. In one preferred embodiment, the human pluripotent stem cell is an embryonic stem cell. In another embodiment the human pluripotent stem cell is a fetal stem cell, such as a primordial germ cell. In another embodiment the human pluripotent stem cell is a adult stem cell. As used herein, the term "pluripotent" refers to a cell capable of at least developing into one of ectodermal, endodermal and mesodermal cells. As used herein the term "pluripotent" refers to cells that are totipotent and multipotent. As used herein, the term "totipotent cell" refers to a cell capable of developing into all lineages of cells. The term "multipotent" refers to a cell that is not terminally differentiated.

One aspect of the present invention includes populations of pluripotent or precursor cells that are capable of selectively, and in some aspects selectively reversibly, developing into different cellular lineages when cultured under appropriate conditions. As used herein, the term "population" refers to cell culture of more than one cell having the same identifying characteristics. The term "cell lineage" refers to all of the stages of the development of a cell type, from the earliest precursor cell to a completely mature cell (i.e. a specialized cell). A "precursor cell" can be any cell in a cell differentiation pathway that is capable of differentiating into a more mature cell. As such, a precursor cell can be a pluripotent cell, or it can be a partially differentiated or reversibly differentiated cell. The term "precursor cell population" refers to a group of cells capable of developing into a more mature or differentiated cell type. The term "progenitor cell" may be used interchangeably with the term "precursor cell." A precursor cell population can comprise cells that are totipotent, cells that are pluripotent, cells that are stem cell lineage restricted (i.e. cells capable of developing into less than all ectodermal lineages, or into, for example, only cells of neuronal lineage), and cells that are reversibly stem cell lineage restricted.

In accordance with the present invention, a population of cells is isolated from the human blastocyst and maintained in culture, while remaining pluripotent. As used herein, the terms "maintain" or "maintenance" refer to the stable preservation of the characteristics of the stem cells when cultured in specific culture conditions. Such characteristics can include the cell morphology and gene expression profiles of the stem cells, which can be determined using the techniques described herein. The term "maintain" can also encompass the propagation of the cells, or an increase in the number of ES cells being cultured. The invention contemplates culture conditions that permit the ES cells to remain pluripotent, while the ES cells may or may not continue to divide and increase in number.

The cell morphology and gene expression profiles of the pluripotent cells of the present invention may vary depending on the feeder cell or on the growth factors present in the culture medium. For example, mouse early primitive ectoderm-like (EPL) cells have decreased expression of the Rex1, L17, and Psc1 genes and increased expression of the Fgf5 and K7 genes compared to the levels of expression of these genes in mouse ES cells, yet the mouse EPL cells are still pluripotent (see WO 99/53021). Therefore the pluripotent cells of certain embodiments of the present invention are fundamentally different than cultures of pluripotent cells heretofore isolated and maintained on prior known culture medium. In a preferred embodiment, the selected feeder cell layer maintains embryonic stem cells, expresses IL-6 and signals through the gp130 pathway. In another preferred embodiment, the feeder cell expresses leukemia inhibitory factor, steel cell factor, and FGF.

As used herein, the terms "develop", "differentiate" and "mature" all refer to the progression of a cell from the stage of having the potential to differentiate into at least two different cellular lineages to becoming a specialized and terminally differentiated cell. Such terms can be used interchangeably for the purposes of the present application. The invention contemplates culture conditions that permit such differentiation to be reversible, such that pluripotency or at least the ability to differentiate into more than one cellular lineage can be selectively regained.

The term "cell" as used herein also refers to individual cells, cell lines, or cultures derived from such cells. A "culture" refers to a composition comprising isolated cells of the same or a different type.

The term "feeder cell" refers to a culture of cells that grows in vitro and secretes at least one factor into the culture medium, and that can be used to support the growth of another cell of interest in culture. As used herein, a "feeder cell layer" can be used interchangeably with the term "feeder cell." A feeder cell can comprise a monolayer, where the feeder cells cover the surface of the culture dish with a complete layer before growing on top of each other, or can comprise clusters of cells. As used herein, the terms "cluster" and "clump" can be used interchangeably, and generally refer to a group of cells that have not been dissociated into single cells. The clusters may be dissociated into smaller clusters. This dissociation is typically manual in nature (such as using a Pasteur pipette), but other means of dissociation are contemplated. The cluster of cells can contain varying numbers of cells, ranging generally from 1 to 50,000 cells, more preferably from 1 to 10,000 cells, more preferably from 1 to 1000 cells, and most preferably from 100 to 1000 cells. In a preferred embodiment, the feeder cell comprises an adherent monolayer. Additionally, the cell of interest may or may not be cultured in direct contact with the feeder cell. For instance, the cell of interest can be co-cultured with the feeder cell in such a manner that the cell of interest is physically separated from the feeder cell by a membrane containing pores, yet the feeder cell still enriches the medium in such a way as to support the growth of the cell of interest.

By "isolated" herein is meant free from at least some of the constituents with which a component, such as a cell, is found in its natural state. More specifically, isolated can mean free from 70%, 80%, 90%, or 95% of the constituents with which a component is found in its natural state.

The invention provides for the culture of a human ES cell with a human feeder cell, wherein the human ES cells can differentiate into cells of more than one lineage. The human feeder cell can comprise a dissociated or isolated primary cell, clusters of primary cells, passaged cells or immortalized cells. In one embodiment, the human feeder cell is selected from the group consisting of a human fibroblast cell, a MRC-5 cell, a human embryonic kidney cell, a mesenchymal cell, an osteosarcoma cell, a keratinocyte, a chondrocyte, a Fallopian ductal epithelial cell, a liver cell, a muscle cell, a cardiac cell, a bone marrow stromal cell, a granulosa cell, a skeletal muscle cell, and an aortic endothelial cell. In the most preferred embodiment the human feeder cell is selected from the group consisting of a skin keloid fibroblast, a granulosa cell, a skeletal muscle cell, a Fallopian ductal epithelial cell and a bone marrow stromal cell. In a preferred embodiment, the fibroblast is a skin keloid cell or a fetal skin fibroblast cell. In a preferred embodiment, the muscle cell is a fetal muscle cell. In a preferred embodiment the cell has the characteristics of the skin keloid fibroblast cell, KEL FIB (ATCC Accession Number CRL-1762) and the bone marrow stromal cell, HS-5 (ATCC Accession Number CRL-11882). Alternatively the bone marrow stromal cell is HS-27 (ATCC Accession Number CRL-2496).

In one embodiment, the human feeder cell layer is mitotically inactivated (e.g. by irradiation or by mitomycin C treatment) to prevent further growth of the cell layer. Alternatively, in another embodiment, the human feeder cell layer is slow growing and does not need to be inactivated. In another embodiment, the human feeder cell layer is genetically transformed and is not capable of being mitotically inactivated. The invention further encompasses a human pluripotent stem cell culture comprising one or more supplemental growth factors. The invention provides that the supplemental growth factor can be derived from a human feeder cell.

According to the present invention, the term "supplemental growth factor" is used in its broadest context and refers to a substance that is effective to promote the growth of a human ES cell, maintain the survival of a cell, stimulate the differentiation of a cell, and/or stimulate reversal of the differentiation of a cell. Further, a supplemental growth factor may be a substance that is secreted by a feeder cell into its media. Such substances include, but are not limited to, cytokines, chemokines, small molecules, neutralizing antibodies, and proteins. Growth factors may also include intercellular signaling polypeptides, which control both the development and maintenance of cells, and the form and function of tissues. In preferred embodiments, the supplemental growth factor is selected from the group consisting of steel cell factor (SCF), oncostatin M (OSM), ciliary neurotrophic factor (CNTF), Interleukin-6 (IL-6) in combination with soluble Interleukin-6 Receptor (IL-6R), a fibroblast growth factor (FGF), a bone morphogenetic protein (BMP), tumor necrosis factor (TNF), and granulocyte macrophage colony stimulating factor (GM-CSF).

The invention encompasses a human pluripotent ES cell culture comprising the human pluripotent ES cell and a human feeder cell conditioned medium. In addition, the invention encompasses a human pluripotent ES cell culture comprising the human pluripotent ES cell and a human feeder cell factor conditioned medium. The invention further encompasses a method for the maintenance of a human pluripotent ES cell culture, comprising culturing selected human ES colonies with a human feeder cell factor. The invention provides that the human feeder cell factor can be purified from the human feeder conditioned medium, and that the human feeder cell factor can be used in a purified form to maintain a human ES cell in a pluripotent state, or at least able to differentiate into cells of more than one cell lineage.

"Conditioned medium" refers to a cell culture medium that is obtained from a culture of a human feeder cell on which human ES cells can be cultured and maintained in a pluripotent state. The feeder cell depletes the conditioned medium of some components, but also enriches the medium with cell-derived material, probably including small amounts of growth factors. The term "human feeder cell factor" as used herein means the cell-derived material that is released into the conditioned medium by the human feeder cell. The cell factor that is released into the cell culture medium is useful in enhancing the growth of human ES cells, or in the maintenance of the human ES cell in a pluripotent state. The human feeder cell factor can be identified and purified using techniques that are known to one skilled in the art, and are described herein.

In a preferred embodiment, the conditioned medium is obtained from a cell that is selected from the group consisting of a human fibroblast cell, a MRC-5 cell, a human embryonic kidney cell, a mesenchymal cell, an osteosarcoma cell, a keratinocyte, a chondrocyte, a Fallopian ductal epithelial cell, a liver cell, a muscle cell, a cardiac cell, a bone marrow stromal cell, a granulosa cell, a skeletal muscle cell, and an aortic endothelial cell. In the most preferred embodiment the human feeder cell is selected from the group consisting of a skin keloid fibroblast, a fetal skin fibroblast cell, a granulosa cell, a skeletal muscle cell, a Fallopian ductal epithelial cell and a bone marrow stromal cell. In a preferred embodiment the skin keloid fibroblast, KEL FIB, has ATCC Accession Number CRL-1762 or is a fetal skin fibroblast cell; and the bone marrow stromal cell, HS-5, has ATCC Accession Number CRL-11882. The conditioned medium may be obtained from a human feeder cell using techniques well known in the art. Generally, a feeder cell on which a human ES cell can be cultured is grown to confluence in cell culture medium. The cell culture medium is harvested daily over several days, centrifuged or filtered to remove cell debris (e.g. passed through a 0.22 micron filter) and frozen at −80° C. The conditioned medium is added to the ES growth medium in empirically determined amounts, as judged by the effect on ES growth and viability. In one embodiment, a conditioned medium of the present invention includes medium recovered from about 4-5 day cultures of human granulosa cells grown in culture medium comprising Knock-out DMEM, FBS, β-mercaptoethanol, non-essential amino acid stock, basic fibroblast growth factor, L-glutamine, human LIF and penicillin-streptomycin. The components comprising the medium and the proportions of these components may be readily altered by one skilled in the art. The medium can further comprise one or more supplemental growth factors. The supplemental growth factor may include, but is not limited to the group consisting of SCF, OSM, CNTF, IL-6 in combination with soluble IL-6R, FGF, BMP, TNF, and GM-CSF. It is within the scope of the present invention that a characteristic of a human feeder cell population is the ability to produce a human feeder cell factor that conditions a medium in such a manner that the conditioned medium is capable of maintaining an ES cell population in a pluripotent state.

The invention further encompasses a human pluripotent ES cell developed by the described methods, and cell lines derived therefrom, including tissues and organs.

In accordance with the present invention, the culture conditions are also important in obtaining and maintaining a pluripotent ES cell population of the present invention. During culturing, variables such as cell density, temperature and $CO_2$ levels can be controlled to maximize the development of populations of ES cells. For example, the density of cells in an ES cell culture can affect the spontaneous differentiation of an ES cell population. As such, the optimum cell density for the growth of an ES cell population is from about 1 ES cell to about 10,000 ES cells per $cm^2$, more preferably from about 1 ES cell to about 2000 ES cells per $cm^2$, and even more preferably from about 100 to about 1000 ES cells per $cm^2$. In one embodiment, the ES cells are cultured as a single cell suspension. The optimum temperature for the development of an ES cell population is from about 32° C. and about 40° C., preferably from about 35° C. and 39° C., with a temperature of 37° C. being even more preferred. The optimum $CO_2$ levels in the culturing environment for the development of ES cell populations is from about 1% $CO_2$ to about 10% $CO_2$, more preferably from about 3% $CO_2$ to about 8% $CO_2$, and even more preferably about 5% $CO_2$.

The population of human pluripotent ES cells can be further cultured in the presence of certain supplemental growth factors to obtain a population of cells that are or will develop into different cellular lineages, or can be selectively reversed in order to be able to develop into different cellular lineages. ES cells may be aggregated into embryoid bodies (EBs) prior to being cultured with said growth factors. EBs may be generated using techniques well known in the art (see e.g. Schuldiner et al., 2000 supra). The ES cells or EBs exposed to supplemental growth factors may develop into any or all of the three germ lines. Preferably the cell lineage induced by the growth factor will be homogeneous in nature. The term "homogeneous," refers to a population that contains more than 80%, 90%, or 95% of the desired cell lineage.

A pluripotent ES cell population is capable of developing into cells of mesodermal cell lineage, of ectodermal cell lineage or of endodermal cell lineage. It is within the scope of the present invention that a method to produce a cell type, such as a mesodermal cell, an ectodermal cell and/or an endodermal cell that includes the steps of: (a) selecting a desired cell type to produce; and (b) culturing an ES cell population of the present invention under conditions suitable to obtain the desired cell type may be identified. Suitable culture conditions for obtaining a desired cell type include culturing the ES cell population in a medium including a growth factor that is able to stimulate the ES cell population to differentiate to the desired cell type(s). For example, an ES cell population can be cultured in a medium including a growth factor capable of promoting the differentiation of the cell population into an ectodermal cell type. A preferred culture condition for obtaining a desired cell type that includes primitive ectodermal cells includes culturing a human ES cell population of the present invention in the presence of conditioned medium from a human feeder cell.

It is within the scope of the present invention that one or more known and/or unknown compounds contained in the feeder cell conditioned medium that are useful for enhancing a cell population of the present invention may be identified. As used herein, the term "enhancing" refers to increasing the growth and numbers, and/or the differentiation (i.e., maturation) of a cell population in the presence compared with in the absence of a compound. Such enhancement may or may not be reversed when the compound is removed from the medium. Such compounds can be identified using any method standard in the art. For example, RNA expression in the cells can be analyzed for the presence or absence of RNA transcripts encoding known compounds by using probes specific for the nucleotide sequence of such compounds. In addition, standard expression cloning techniques (as described in Sambrook et al., supra, 1989) to identify nucleic acid sequences encoding both known and unknown compounds can be used.

It is within the scope of the present invention that a conditioned medium of the present invention can be used to identify one or more known and/or unknown compounds contained in the conditioned medium that are useful for enhancing a cell population or maintaining a cell population of the present invention. Such compounds can be identified using any method standard in the art. For example, immunoassays can be used to identify the presence of known compounds in a conditioned medium of the present invention. Alternatively, standard biochemical protein separation techniques (e.g., antibody binding studies, gel electrophoresis and various chromatography techniques, in particular HPLC, known to those of skill in the art) can be used to identify and isolate individual or families of proteins from a conditioned medium. Various types of cell growth assays are applicable in this situation and any cell population of the present invention can be employed in such assays.

It is also within the scope of the present invention that a conditioned medium of the present invention can be used to enhance precursor populations of cells, preferably human pluripotent stem cells. As such, a conditioned medium of the present invention is capable of enhancing the growth and/or differentiation of a cell population including pluripotent and/or stem cell lineage restricted cells. Enhancement of precursor populations of cells is particularly useful in the treatment of diseases that involve replenishing precursor cell populations in a subject. For example, Parkinson's patients are preferred recipients of precursor cell populations enhanced using a conditioned medium of the present invention.

Precursor cell populations can be enhanced by culturing such cells under suitable culture conditions in the presence of an effective amount of conditioned medium. One can determine the culture conditions and amount of conditioned medium to use based upon certain parameters, such as the cell type being expanded, the health of the cells being expanded and the extent of expansion required. The enhancement can be determined by examining the gene expression profile of the cell population, or of an individual cell. The gene expression profile can be determined using techniques well known in the art, for example, using RT-PCR, Northern blotting, or subtractive hybridization.

The scope of the invention also includes an enhanced precursor cell population, comprising a precursor cell population (i.e. a population of cells comprising precursor cells) contacted with a conditioned medium of the present invention, wherein the step of contacting results in the formation of an enhanced precursor population. Preferably, an enhanced precursor cell population comprises about 2-fold, more preferably about 10-fold and even more preferably about 50-fold more cells than the precursor cell population. A particularly preferred precursor cell population comprises a human pluripotent stem cell population.

According to the present invention, a population of immortalized precursor cells is preferably at least about 70% clonal, more preferably at least about 80% clonal and even more preferably at least about 90% clonal. As used herein, the term "clonal" refers to a group of cells that all derive from a single parental cell, and thus should be genetically identical.

The pluripotent and/or precursor cell populations of the present invention can be used in the isolation and evaluation of embryonic cell compounds. As used herein, an "embryonic cell compound" is a compound associated with the selective differentiation of embryonic cells. Thus, another aspect of the present invention is a method to identify a compound expressed during the development of a population of ES cells. The method comprises characterizing at least a portion of the cellular composition of at least one cell contained in a population of cells including an ES cell population, or a partially or fully differentiated ES cell-derived population of the present invention, to identify a compound expressed during the development of a population of ES cells. As used herein, a cellular composition refers a composition containing components of a cell. Preferred cellular compositions of the present invention include nucleic acids, proteins, lipids (including membranes) and/or carbohydrates, with proteins, DNA molecules and RNA molecules being more preferred.

The present invention includes a variety of methods to identify an embryonic cell compound using an embryonic cell population of the present invention. In one embodiment, an embryonic cell compound of the present invention is identified by direct hybridization studies, comprising hybridizing a nucleic acid molecule probe (which can be DNA, RNA or modified forms thereof) to a composition of nucleic acid molecules isolated from an embryonic cell population of the present invention. Such a method is useful for identifying the expression of compounds in an embryonic cell population. For example, a nucleic acid molecule encoding a protein can be hybridized under suitable conditions known to those of skill in the art (see, for example, Sambrook et al., 1989 supra) to an RNA composition isolated from an embryonic cell population of the present invention, or to a cDNA product thereof. Preferred nucleic acid molecules for use in a direct hybridization study of the present invention include nucleic acid molecules that encode marker proteins including, but not limited to, ectodermal cell proteins, mesodermal cell proteins, endodermal cell proteins, and/or human pluripotent ES cell proteins. Respective examples of ectodermal, mesodermal and endodermal cells include, but are not limited to neural crest and neurectoderm cells; skeletal muscle, bone and hematopoietic cells; and tissues derived from the primitive gut such as hepatic parenchymal cells and pancreatic cells. As used herein, a marker protein is a protein typically found in certain cell types and, as such, can suggest identification of such cell type. An embryonic cell-derived nucleic acid composition useful for such direct hybridization studies can include genomic DNA, RNA or cDNA of such RNA.

In another embodiment, an embryonic cell compound of the present invention is identified by selective nucleic acid hybridization techniques well known to those of skill in the art. Such subtractive hybridization techniques are particularly useful for identifying novel embryonic cell compounds and for identifying compounds expressed in a given cell type. Subtractive hybridization techniques of the present invention can be performed by, for example: (1) hybridizing nucleic acid molecules isolated or derived from an embryonic cell population of the present invention to nucleic acid molecules isolated or derived from a non-embryonic cell population; or (2) hybridizing nucleic acid molecules isolated or derived from a first embryonic cell population of the present invention to nucleic acid molecules isolated or derived from a second embryonic cell population. For example, nucleic acid molecules isolated from an ES cell population cultured with human liver cells can be subtracted from nucleic acid molecules isolated or derived from an ES cell population cultured with mouse embryonic fibroblasts.

In yet another embodiment, an embryonic cell compound of the present invention is identified by nucleotide sequencing of DNA isolated from an embryonic cell population of the present invention. In order to identify compounds expressed in certain cell types, cDNA copies of poly A+ RNA is preferably analyzed. Identification of embryonic cell compounds can be achieved by comparing the DNA sequence information encoding such compounds derived from the embryonic cell population with sequences of known molecules. Such DNA sequencing studies are particularly useful for identifying novel embryonic cell compounds. DNA sequencing studies can be performed using techniques standard in the art (see, for example, Sambrook et al., 1989 supra.).

In yet another embodiment, an embryonic cell compound of the present invention is identified by selective binding of proteins isolated from an embryonic cell population of the present invention to antibodies specific for known cellular proteins to determine the presence of such cellular proteins in the embryonic cell population. Such antibody binding studies are particularly useful for identifying the expression of known compounds by embryonic cell populations of the present invention. Antibody binding studies of the present invention can be performed using techniques standard in the art, such as by immunoblot assays, immunoprecipitation assays, enzyme immunoassays (e.g., ELISA), radioimmunoassays, immunofluorescent antibody assays and immunoelectron microscopy; see, for example, Sambrook et al., 1989 supra.

In yet another embodiment, an embryonic cell compound of the present invention is identified by cell culture assays that indicate cell survival and cell proliferation. Such cell culture assays are particularly useful for identifying both novel and known growth factors that are secreted by an embryonic cell population of the present invention. A cell culture assay of the present invention can be performed by: (1) recovering supernatant from a culture of a dense embryonic cell population of the present invention; (2) contacting the supernatant with a sparse population of the embryonic cell population; and (3) determining if the supernatant is able to promote the survival and/or proliferation of said embryonic cell population by observing the health of said cell population. Such cell culture assays can be performed using the cell culturing techniques disclosed in detail herein. A preferred dense population of cells includes any cell density used to culture an embryonic cell population as disclosed herein. A preferred sparse population of an embryonic cell population of the present invention includes a cell density of from about 1 to about 1000 cells per $cm^2$.

In yet another embodiment, an embryonic cell compound of the present invention involved in signal transduction in an embryonic cell is identified using kinase assays that are standard in the art. Such kinase assays are particularly useful for identifying known signal transduction proteins in an embryonic cell population of the present invention.

In yet another embodiment, an embryonic cell compound of the present invention is identified by protein:protein binding studies other than antibody binding studies. In particular, embryonic cell compounds are identified by determining ligand:receptor interactions. For example, an embryonic cell population of the present invention can be contacted with a known ligand to determine if the cell population contains cells having the receptor to which the ligand can bind. Such protein:protein binding studies can be performed using techniques known to those of skill in the art.

According to the present invention, an embryonic cell compound can be a compound that has been previously identified, or not previously identified, from a cell or culture medium of a cell other than a population of cells of the present invention. For example, an embryonic cell compound of the present invention can include a growth factor that is also produced by a more mature fetal or adult cell of an animal.

An embryonic cell compound of the present invention can be a compound that is capable of having a biological effect on a cell. For example, preferred embryonic cell compounds are capable of maintaining the survival of a cell, including possibly inducing the propagation of a cell, or stimulating the differentiation of a cell. Preferred embryonic compounds of the present invention include a compound that can be used as a marker for a population of embryonic cells. In particular, such markers for a population of embryonic cells can be cell surface markers, secreted molecules, cytoplasmic signal transduction molecules, transcription factors and other DNA or RNA binding proteins. Known markers of pluripotent ES cells include stage specific embryonic antigen (SSEA)-1, SSEA-3, SSEA-4, TRA-1-60, TRA-1-81, Oct-4 and alkaline phosphatase. The patterns of these markers vary between species. The cells of the present invention may or may not express such markers. As used herein, a "cell surface marker" refers to any compound on the surface of a cell that is detectable by techniques such as antibody binding studies, gel electrophoresis and various chromatography techniques known to those of skill in the art. A cell surface marker can include cell surface receptors, adhesion proteins, cell surface carbohydrate moieties, membrane-bound ligands and other molecules involved in cell-to-cell communication. A secreted molecule refers to any molecule produced and secreted by a cell into an extracellular environment and includes growth factors and other ligands. A cytoplasmic signal transduction molecule refers to a molecule that is able to regulate an intercellular chemical reaction that enables a cell to modify its biological functions based on signals in the environment, either outside or inside the cell. Signal transduction molecules can include enzymes, such as kinases, phosphatases and phospholipases. Preferred embryonic cell compounds of the present invention include a cell surface receptor, a cell surface molecule, a cytoplasmic signal transduction protein, a transcription factor, a growth factor, and DNA or RNA binding proteins.

Identification of known and novel (i.e. newly identified) compounds in an embryonic cell population of the present invention is particularly useful for defining markers useful for the identification and/or isolation of comparable populations of cells from non-embryonic populations of cells. A particularly preferred non-embryonic cell population to look for cells having embryonic markers includes non-embryonic cell populations, including neurons. The presence of an embryonic cell marker of the present invention on a non-embryonic cell can indicate that the non-embryonic cell is pluripotent. Preferred embryonic cell population markers to identify comparable non-embryonic cell populations include lineage-specific markers, such as early primitive ectoderm-like precursor markers.

One embodiment of the present invention is a formulation that contains one or more isolated embryonic cell compounds of the present invention that can be used for therapeutic or experimental use. According to the present invention, an isolated embryonic cell compound is a compound that has been removed from its natural milieu. An isolated embryonic cell compound can, for example, be obtained from its natural source, be produced using recombinant DNA technology, or be synthesized chemically. Preferred embryonic cell compounds of the present invention, including homologues thereof, are capable of regulating embryonic development. A preferred embryonic cell compound homologue includes at least one epitope capable of effecting differentiation of an ES cell population. The ability of an embryonic cell compound homologue to effect differentiation of an ES cell Population can be tested using techniques disclosed herein.

Another aspect of the present invention comprises an antibody capable of binding to a cell compound of a cell population of the present invention. Binding can be measured using a variety of methods known to those skilled in the art including immunoblot assays, immunoprecipitation assays, enzyme immunoassays (e.g., ELISA), radioimmunoassays, immunofluorescent antibody assays and immunoelectron microscopy; see, for example, Sambrook et al., supra, 1989. Antibodies of the present invention can be either polyclonal or monoclonal antibodies. Antibodies of the present invention include functional equivalents such as antibody fragments and genetically-engineered antibodies, including single chain antibodies that are capable of selectively binding to at least one of the epitopes of the protein or mimetope used to obtain the antibodies. Preferred antibodies are raised in response to surface marker proteins of an embryonic cell population of the present invention, in particular, surface cell receptors. Antibodies of the present invention can be produced using methods standard in the art. Antibodies of the present invention are particularly useful for identifying and isolating populations of cells having such surface markers, in particular, populations of embryonic cells from different species of animals and/or cells with similar markers from adult bone marrow. Thus, particularly preferred antibodies of the present invention include antibodies that are capable of binding to cellular markers that delineate between different embryonic cell populations of the present invention.

Another aspect of the present invention is a therapeutic composition that comprises a pluripotent cell population of the present invention, which is capable of serving as a population of cells that act as progenitors of various lineages. The therapeutic composition can be particularly useful to repopulate one or more lineages in an animal. As used herein, the term "repopulate" refers to a cell population that can be administered to an animal to restore a lineage of cells. A therapeutic composition of the present invention can be useful for the treatment of disease, such as Parkinson's and Alzheimer's diseases and other neurodegenerative disorders, spinal cord injuries, stroke, macular degeneration, burns, liver failure, heart disease, diabetes, Duchenne's muscular dystrophy, osteogenesis imperfecta, osteoarthritis, rheumatoid arthritis, anemia, leukemia, breast cancer and other solid tumors, and AIDS.

A therapeutic composition of the present invention can be particularly useful for enhancing populations of neuronal cells used in transplantation procedures to treat Parkinson's disease.

In one embodiment, the present invention includes a method to supplement a neuronal cell population in an animal, comprising administering to an animal a suitable number of cells of a pluripotent cell population of the present invention. A suitable number of cells include a number needed to, for example, repopulate a neuronal population in a subjected being treated for Parkinson's disease. Preferably, the administration of a suitable number of cells ameliorates or modifies the symptoms of the disease.

Therapeutic compositions of the present invention can be administered to any animal, preferably to mammals, and more preferably to humans. Therapeutic compositions of the present invention can be formulated in an excipient that the animal to be treated can tolerate and that maintains the integrity of the embryonic cell population. Examples of such excipients include aqueous physiologically balanced salt solutions. Excipients can also contain minor amounts of additives, such as substances that enhance isotonicity and chemical stability.

According to the present method, the step of assessment can be performed using any one of a variety of methods known to those of skill in the art. In particular, the assessment step can be performed using a proliferation assay and/or a differentiation assay. A preferred proliferation assay of the present invention comprises standard assays that determine cell count number, thymidine uptake by a cell and enzyme activity, including enzyme-linked immunoassays and cellular enzyme assays. A preferred differentiation assay of the present invention comprises a standard method including: (a) determining Oct-4 gene expression; (b) identifying cell surface markers; (c) determining responsiveness to a growth factor; (d) observing alterations in morphology; and (e) determining expression of genes associated with differentiation of neuronal cells.

Another aspect of the present invention is the use of a cell population of the present invention for the treatment of genetic diseases. Genetic diseases associated with various lineages can be treated by genetic modification of autologous or allogenic populations of embryonic cells of the present invention. For example, diseases such as beta-thalassemia, sickle cell anemia, adenosine deaminase deficiency and other genetic diseases related to a deficiency or malfunction of a cell of hematopoietic lineage, can be corrected by introduction of a wild type gene into the embryonic cell population. Diseases other than those associated with hematopoietic cells can be treated, where the disease is related to the lack of a particular secreted product, such as a hormone, enzyme, growth factor and the like. Specific promoters can be employed based upon identification of transcription factors of an embryonic cell population as described herein. Thus, inducible production of a desired product encoded by transformed genes can be achieved. Methods for transformation and expression of genes in an embryonic cell population of the present invention are standard to those in the art (see, for example, Sambrook et al., supra, 1989).

In accordance with the present invention, a nucleic acid molecule can be transformed into an embryonic cell population of the present invention to inhibit particular gene products, thereby inhibiting susceptibility to a disease. For example, an embryonic cell population of the present invention can be transformed with a ribozyme, or a nucleic acid molecule that is capable of homologous recombination or antisense expression.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Isolation of a Human Pluripotent ES Cell on a Mouse Embryonic Fibroblast Feeder Cell Layer Embryo Collection: Human embryos were obtained as described by Thomson et al., 1998, supra. Briefly, fresh or frozen cleavage stage human embryos were produced by in vitro fertilization (IVF) for clinical purposes. The embryos were donated by individuals after informed consent and after institutional review board approval. The donated human embryos were cultured to the blastocyst stage in IVC-1 Medium (In Vitro Care, San Diego, Calif.) from day 0 until day 3 or day 4. After 3 days of culture the embryos were visually assessed by qualified embryologists for their quality and likely ability to develop normally. Embryos of high quality were transferred either to the patients from whom the ova were collected or were donated to other patients. The remaining embryos were cultured in IVC-3 blastocyst medium (In Vitro Care, San Diego, Calif.) and reassessed at 5 days in vitro. High quality embryos were frozen for future use, while the embryos used in this study were those assessed to be of such poor quality as to have no likelihood of normal development. In another embodiment, the use of high quality embryos is anticipated.

Isolation of cells from the inner cell mass: Immunosurgery was performed on the blastocysts in order to isolate the inner cell masses (ICMs). The zona pellucida was removed by digestion in pronase (Sigma 2 mg/ml) in blastocyst IVC-3 culture medium containing BSA (fraction V 3 mg/ml). The embryos were subsequently exposed to a 1:7 dilution of anti-human placental alkaline phosphatase antibody in IVC-3/BSA for 45 minutes at 37° C. The embryos were washed three times in IVC-3/BSA for 5 minutes, and were then incubated in Guinea pig complement (Gibco, BRL) in IVC-3 for 5 minutes at a 4:1 dilution. After five further washes in IVC-3/BSA, the lysed trophoblast cells were removed from the ICMs by gentle pipetting. The ICMs were plated on mouse embryonic fibroblasts (MEFs) inactivated with 10 µg/ml Mitomycin C (Sigma). The procedure to inactivate the MEFs was described previously (Robertson, E., ed. *Teratocarcinomas and Embryonic Stem Cells: A Practical Approach*, Oxford: IRL Press, 1987).

The ICMs plated on the MEFs formed ICM-derived cell masses after 6-10 days in culture. The ICM-derived cell masses were isolated from the endoderm outgrowths with a micropipette. The cells were then dissociated by gentle pipetting through a flame polished micropipette. The dissociated cells were re-plated on fresh MEFs. The cells were later observed for colony formation. Colonies of cells that had the appearance of pluripotent ES cells were selected and isolated using a micropipette. The morphological features that were sought included a high nucleus/cytoplasm ratio, and prominent nucleoli. The selected cells were then cultured on MEF feeder cell layers.

MEF feeder cell layer preparation: MEF feeder cell layers were established at a density of 18,000 to 300,000 cells per $cm^2$. MEFs were prepared from mouse fetuses at 13.5 days of gestation, as described previously (Robertson, 1987 supra). After the establishment of the primary MEF cultures, the MEF cells were passaged once before freezing. The frozen cell stocks were thawed into tissue culture flasks and were mitotically inactivated using mitomycin C as described above. After thoroughly washing the mitotically inactivated cells five times with Dulbecco's modified Eagle's medium (DMEM; Gibco, BRL) containing 10% fetal bovine serum (FBS; HyClone), the culture medium was changed to HES medium. We have found it beneficial to culture the inactivated cells for at least three days before using the cells as feeder layers for HES cells.

HES Medium: The culture medium used for human ES cells consists of Knock-out DMEM or DMEM/F12 (1:1) (Gibco, BRL), plus 20% FBS (HyClone) or 15% FBS and 5% KRS (Gibco-BRL), 0.1 mM β-mercaptoethanol, 1% non-essential amino acid stock (Gibco, BRL), 4 ng/ml basic fibroblast growth factor (bFGF; Sigma), 1 mM L-glutamine (Gibco, BRL), 1000 units/ml human LIF (Chemicon) and 50 units-50 µg/ml of penicillin-streptomycin.

Cryopreservation: Cells were frozen in HES culture medium with 10% DMSO and 5-50% FBS in liquid nitrogen.

Cell Manipulation and passaging: Using the above described methods, four separate human ES cell lines were derived from a total of 23 non-viable blastocysts. All of the cell lines remained undifferentiated for at least two months in culture, and have been frozen and successfully thawed. To passage a human ES cell line, Pasteur pipettes were used to individually select colonies, mechanically dissociate the colonies into clumps, and transfer clusters of about 50-100 human ES cells to fresh culture dishes and MEF feeder cell layers.

Example 2

Characterization of a Human Pluripotent ES Cell Isolated on MEFs

The human ES cell lines that were generated in Example 1 were characterized to ensure that they were pluripotent.

Morphology: The morphology of the derived human ES cell was similar in at least some ways to the human ES cell lines derived by other investigators (Thomson et al., 1998 supra; Reubinoff et al., 2000 supra). The human ES cells have a high nucleus/cytoplasm ratio and prominent nucleoli. Additionally, the borders between the individual ES cells are very distinguishable, particularly in comparison to mouse ES cells. The characteristic morphology of human ES cells allows for the ready identification of the cells.

Gene expression studies: The human ES cell lines generated in Example 1 expressed alkaline phosphatase and Oct-4, two molecular markers of pluripotent cells.

Alkaline phosphatase was visualized using the Vector Red alkaline phosphatase substrate kit (Vector Lab, Burlingame, Calif.). The kit was used according to the manufacturer's specifications. Briefly, growth medium was aspirated from the cells, the cells were washed once with DPBS, and the substrate working solution was applied. The cells were incubated with the substrate solution for a period of 15-20 minutes in the dark. The cells were then analyzed for alkaline phosphatase staining with both phase contrast and fluorescence microscopy.

Total RNA was isolated using the RNAqueous-4 PCR Kit (Ambion) according to the manufacturer's specification. Briefly, Pasteur pipettes were used to manually isolate the human ES cells from the feeder layer. The ES cells were washed twice in DPBS, and the RNA was isolated immediately, or the cells were then frozen. In order to isolate RNA, the ES cells were harvested by centrifugation and resuspended in the lysis-binding solution. An equal volume of 64% ethanol solution was added. This mixture was applied to a filter cartridge and centrifuged at maximum speed for 1 minute. The filter with RNA on it was washed once with 700 µl of wash solution 1. The filter was then washed with 500 µl of wash solution 2/3. The filter was washed with a second 500 µl aliquot of wash solution 2/3 and then an additional centrifugation step was carried out to ensure complete removal of all wash solutions. RNA was then eluted in a two-step manner with elution solution that had been pre-heated to 95-100° C. An aliquot of 40-60 µl of elution solution was applied to the filter cartridge, which was then spun at maximum speed for 1 minute, and the RNA was collected in a clean microcentrifuge tube. A second aliquot of elution solution was added and RNA was again collected in the same tube. After elution, the optional DNase I Treatment and DNase Inactivation protocol was followed. A total of 0.1 volumes of 10× DNase I buffer, and 1 µl of DNase I were added to the samples, and the samples were then incubated for 15-30 minutes at 37° C. After DNase I treatment, a total of 0.1 volumes of DNase inactivation reagent was added to the samples. This mixture was incubated at room temperature for two minutes. The DNase inactivation reagent was then pelleted by centrifugation and the solution containing DNA free RNA was removed and put into a sterile microcentrifuge tube.

RT-PCR was carried out using the Perkin Elmer Gene Amp RNA PCR kit according to manufacturer's specifications. Briefly, 2 µl of RNA was reverse transcribed using the MuLV reverse transcriptase, oligo dT primer, buffers, and reagents that were provided in the kit. The reverse transcription yielded 20 µl of cDNA per sample to be analyzed, which was then subjected to PCR using the provided Taq polymerase, buffers, and reagents. PCR primers were designed to detect Oct-4 expression. The primers were based on the human Oct-4 sequence and amplified a 350 bp fragment of DNA. The forward primer was 5'-CTCCTGGAGGGCCAGGAATC-3' (SEQ ID:1) and the reverse primer was 5'-CCACATCGGC-CTGTGTATAT-3' (SEQ ID:2). As a control, expression of human G3 PDH was assayed using primers described previously (Schuldiner et al., 2000 supra). The forward primer was 5'-TGAAGGTCGGAGTCAACGGATTTGGT-3' (SEQ ID NO:3) and the reverse primer was 5'-CATGTGGGCCAT-GAGGTCCACCAC-3' (SEQ ID NO:4). The G3 PDH primers amplified an 890 bp fragment. PCR was carried out for 40 cycles at the following conditions: denaturation for 40 seconds at 94° C., annealing for 40 seconds at 55° C., and extension for 90 seconds at 72° C. PCR was performed in a Biometra T Gradient PCR machine. The PCT products were separated on a 1% agarose gel and visualized by ethidium bromide staining.

Cell surface antigens: Mouse ES cells have a characteristic expression pattern of cell surface antigens, which differs from the expression pattern of cell surface antigens on human ES cells (summarized in TABLE 1) (reviewed in Pera et al., 2000 supra). TABLE 1 additionally shows the patterns of cell surface antigens on undifferentiated rhesus ES cells, and differentiating rhesus ES cells.

Human ES cells were assayed for the presence of several cell surface markers whose patterns have been defined for ES cells. The antibodies used included stage specific embryonic antigen (SSEA)-1, 3, and 4 as well as TRA-1-60 and TRA-1-81. SSEA-1, 3 and 4 were obtained from the Developmental Studies Hybridoma Bank of the National Institute of Child Health and Human Development. TRA-1-60 and TRA-1-81 were a generous gift of Dr. Peter Andrews. Primary antibodies were detected using fluorescent conjugated secondary antibodies, and signals were visualized using fluorescent microscopy. It shall be understood that other antibodies for these same cell markers can be generated, and additionally, other detection systems can be readily substituted.

Mouse ES cells can be used as a positive control for SSEA-1, and a negative control for SSEA-3, SSEA-4, TRA-1-60, and TRA-1-81. Other routine negative controls include the omission of the primary or the secondary antibody, and the substitution of the primary antibody with an antibody that has no specificity for the tissue.

TABLE 1

| Cell Surface Marker | Human ES cells | Mouse ES cells | Rhesus ES cells | Differentiating Rhesus ES cells |
|---|---|---|---|---|
| SSEA-1 | − | + | − | − |
| SSEA-3 | +[#] | − | −/+ | − |
| SSEA-4 | +++* | − | +++ | − |
| TRA-1-60 | +++ | − | +++ | + |
| TRA-1-81 | +++ | − | +++ | N/A |
| Oct-4 | +++ | +++ | +++ | N/A |

[#]indicates weak staining
*indicates strong staining
N/A indicates that the experiment was not performed Example 3

Maintenance of a Human Pluripotent ES Cell on a Human Granulosa Feeder Cell Layer Isolation of granulosa cells: Human granulosa cells were harvested at the time oocytes were collected for IVF. The oocytes were collected by laporoscopy. Oocytes have a tightly associated layer of cells surrounding them, known as the cumulus oophorus. The granulosa cells that comprise the cumulus oophorus were stripped from the oocytes by hyaluronidase treatment. The hyaluronidase treatment was followed by repeated passage of the granulosa cells through a narrow bore pipette. The granulosa cells were isolated as clumps of cells, which were further broken down to a single cell suspension by a 2 minute trypsin-EDTA treatment with 0.25% trypsin-EDTA in PBS (Gibco-BRL). After the trypsin treatment, the granulosa cells were washed with HES cell medium and plated on tissue culture dishes. The granulosa cells were cultured at 37° C. and 5% $CO_2$.

The granulosa cells were cultured in HES medium. After 7-10 days the cells started to proliferate. When the granulosa cells reached confluence, the monolayer was used as a cell feeder layer for the culture of the human ES cell. The granulosa cells were not mitotically inactivated, however, in a preferred embodiment the granulosa cells can be mitotically inactivated.

Co-culture of granulosa and human ES cells: To test the ability of the granulosa cells to support the growth, and to prevent differentiation of the human ES cell, the isolated human ES cell line was collected from its standard growth conditions on MEFs, as described in Example 1. Clumps of human ES cells were re-plated onto the granulosa cell monolayer. The clumps usually consisted of 10-1000 cells, where the typical number of cells per clump was approximately 100. 5-50 clumps were plated on the granulosa cell monolayer, where the typical number of clumps plated was around 20. The human ES cells attached to the monolayer of granulosa cells within one day after plating, as determined by visual inspection. Three days after the cells attached, the human ES cell colonies were fixed and examined for alkaline phosphatase activity as described in Example 2. The human ES cell line co-cultured with human granulosa cells expressed alkaline phosphatase, indicating that the human ES cells were still pluripotent.

The human ES cell line co-cultured with the human granulosa feeder cell layer is characterized to ensure pluripotency using tests well known in the art. For example, alkaline phosphatase expression is determined. Other indicators of pluripotency are also investigated. These include, but are not limited to, karyotype analysis; the presence of stage specific embryonic antigens such as SSEA-1 (Solter, D. and B. Knowles, Proc. Natl. Acad. Sci. USA 75: 5565-5569, 1978), SSEA-3, SSEA-4 (Kannagi, R., et al, Embo J. 2:2355-2361, 1983) and epitopes recognized by the antibodies TRA-1-60 (ATCC HB-4783) and TRA-1-81 (ATCC HB-4784) (Andrews, P., et al., 1984 supra); in vitro differentiation into cell types from all three germ cell layers; DBHB antibody data; and the ability of these cells to form teratocarcinomas or teratomas when injected into immuno-compromised (SCID) mice. The other indicators of pluripotency are consistent with previously reported results for human ES cells (Thomson, 1998 supra), and provide evidence that the human ES cell lines maintained on a human granulosa cell layer are pluripotent.

The culture conditions for the co-culture of granulosa cells with human ES cells are optimized to maintain human ES cells in a pluripotent state for indefinite periods of time (e.g. greater than 1 year). Granulosa cells are obtained from patients who are not undergoing IVF treatment, and are not being treated with high doses of hCG or LH, which have been implicated in inducing apoptosis in granulosa cells. (Zhang et al., 2000 Mol. Hum. Reprod., 6(2):146-53). Alternatively, FSH is added to the culture medium, since FSH induces proliferation and steroid production in granulosa cells. Finally, cultures are established from clusters of granulosa cells rather than from a single cell suspension, since the technique used to generate a single cell suspension is likely to be deleterious to granulosa cells (Slavinsid-Turley and Auersperg, 1978 Journal Endocrinology. September;78(3):427-34).

Example 4

Isolation and Maintenance of a Human Pluripotent ES Cell on a Human Granulosa Feeder Cell Layer Except as outlined below, all of the materials and methods are described in Examples 1-3.

Human embryos are obtained as described in Example 1. The ICM of the embryo is isolated using the technique described in Example 1, or using other techniques that are well known in the art. The ICM is plated onto and allowed to attach to a human granulosa feeder cell layer. The human granulosa feeder cell layer is generated as described in Example 3. After 7-30 days, ICM-derived masses are isolated and dissociated as described in Example 1. The dissociated cells are re-plated on a fresh human granulosa feeder cell layer. Colonies of cells with the morphology characteristic of human pluripotent ES cells are isolated and re-plated as described in Example 1, except the cells are plated on a human granulosa feeder cell layer. The resulting ES cells are routinely passaged using techniques well known in the art.

The human ES cell line co-cultured with the human granulosa feeder cell layer is characterized to ensure pluripotency using tests well known in the art. For example, alkaline phosphatase expression is determined. Other indicators of pluripotency are also investigated. These include, but are not limited to, karyotype analysis; the presence of stage specific embryonic antigens such as SSEA-1 (Solter, D. and B. Knowles, Proc. Natl. Acad. Sci. USA 75: 5565-5569, 1978), SSEA-3, SSEA-4 Kannagi, R., et al., Embo J. 2:2355-2361, 1983) and epitopes recognized by the antibodies TRA-1-60 (ATCC HB-4783) and TRA-1-81 (ATCC HB-4784) (Andrews, P., et al., Hybridoma 3:347-361, 1984), in vitro differentiation into cell types from all three germ cell layers; DBHB antibody data; and the ability of these cells to form teratocarcinomas or teratomas when injected into immuno-compromised (SCID) mice. The other indicators of pluripotency are consistent with previously reported results, and provide evidence that the human ES cell lines isolated and maintained on human granulosa feeder cell layers are pluripotent.

The conditions for the isolation and maintenance of a human ES cell on a human granulosa feeder cell layer are optimized so to maintain human ES cells in a pluripotent state for indefinite periods of time (e.g. greater than 1 year). The culture conditions are optimized by changing the culture medium, varying the temperature, varying the concentrations of the human ES cell or the feeder cell, adding different supplemental growth factors, mitotically inactivating the feeder cell layer, and changing the presence or concentrations of fetal bovine serum or serum substitutes.

Example 5

Maintenance of a Human Pluripotent ES Cell on a Human Granulosa Cell Factor Conditioned Medium Except as outlined below, all of the materials and methods are described in Examples 1-4.

Human embryos are obtained as described in Example 1, and human pluripotent ES cells are obtained as described in any of Examples 1-4. The dissociated ICM-derived cells are re-plated without a feeder cell layer, in the presence of conditioned medium.

The conditioned medium is obtained from a human granulosa feeder cell. The human granulosa feeder cell is generated as described in Example 3. The conditioned 80 medium is collected from confluent 4-5 day human granulosa cell cultures. The human granulosa cell may be a primary cell, or an immortalized cell. In one embodiment, the human granulosa cell is mitotically inactivated prior to the collection of the medium. The human granulosa cells and cell-debris are removed from the culture medium, where the removal is typically by centrifugation or filtration. The human granulosa cell releases a soluble cell factor into the conditioned medium that is not removed by the centrifugation or filtration process. The conditioned medium is useful in promoting the growth of an ES cell, maintaining the survival of the ES cell in a pluripotent state, stimulating the differentiation of a human embryonic stem cell, and/or stimulating reversal of the differentiation of a cell.

The conditioned medium is added to the human ES cells in an amount that is empirically determined to maintain the ES cell in the desired pluripotent or selectively differentiated state. The state of the human ES cell is determined using tests and markers well known in the art, and described herein.

Example 6

Maintenance of a Human Pluripotent ES Cell on a Human Muscle Feeder Cell Layer

Except as outlined below, all of the materials and methods are described in Examples 1-5.

Isolation of human feeder cells: Human muscle feeder cells are obtained from commercial sources, or are obtained through biopsies of human tissues. In a preferred embodiment, the human muscle cell is a skeletal muscle cell. In certain embodiments the skeletal muscle cell is fetal, or neonatal. In other embodiments the skeletal muscle cell is obtained from an adult. In one embodiment the skeletal muscle cell is a cell line. In another embodiment, the human skeletal muscle feeder cell is a primary cell, wherein the primary cell is obtained from a biopsy. Further, human feeder cell can be mitotically inactivated prior to culturing the stem cell with the feeder cell layer.

Primary muscle cell lines are established from biopsies of human tumors, or other tissues. Generally, the biopsy tissue is dissociated using chemical means (i.e. trypsin, chymotrypsin, etc.) and physical means (i.e. passage through a narrow bore pipette). The cells can be further dissociated into a single cell suspension by a treatment with trypsin-EDTA. After dissociation, the primary cells are washed and plated on tissue culture dishes. The human muscle feeder cells are generally cultured at 37° C. and 5% $CO_2$.

The human feeder cells are cultured in HES medium, which is altered to optimize the growth of each feeder cell. Alternatively, the muscle cells are cultured in a medium optimized for the growth of muscle cells. When the feeder cell is subconfluent or reaches confluence, the monolayer is used as a cell feeder layer for the culture of the human stem cell.

Co-culture of human feeder cells and human ES cells: To test the ability of the human feeder cells to support and maintain the human ES cell, the isolated human ES cell line is collected from its standard growth conditions on MEFs, as described in Example 1. Clumps of human ES cells are re-plated onto the human feeder cell monolayer. The clumps usually consist of 10-1000 cells, where the typical number of cells per clump is approximately 100. 5-50 clumps are plated on the cell monolayer, where the typical number of clumps plated is around 20. The human ES cells are visually inspected to ensure that they attach to the monolayer of human feeder cells.

The human ES cell line co-cultured with the human muscle feeder cell layer is characterized to ensure pluripotency using tests well known in the art. For example, alkaline phosphatase expression is determined. Other indicators of pluripotency are also investigated. These include, but are not limited to, karyotype analysis; the presence of stage specific embryonic antigens such as SSEA-1 (Solter, D. and B. Knowles, Proc. Natl. Acad. Sci. USA 75: 5565-5569, 1978), SSEA-3, SSEA-4 (Kannagi, R., et al, Embo J. 2:2355-2361, 1983) and epitopes recognized by the antibodies TRA-1-60 (ATCC HB-4783) and TRA-1-81 (ATCC HB-4784) (Andrews, P., et al., 1984 supra); in vitro differentiation into cell types from all three germ cell layers; DBHB antibody data; and the ability of these cells to form teratocarcinomas or teratomas when injected into immuno-compromised (SCID) mice. The other indicators of pluripotency are consistent with previously reported results for human ES cells (Thomson, 1998 supra), and provide evidence that the human ES cell lines maintained on a human skeletal muscle cell feeder layer are pluripotent.

The culture conditions for the co-culture of human skeletal muscle feeder cells with human ES cells are optimized to maintain human ES cells in a pluripotent state for indefinite periods of time (e.g. greater than 1 year). The culture conditions are optimized by changing the culture medium, varying the temperature, varying the concentrations of the human ES cell or the feeder cell, adding different supplemental growth factors, mitotically inactivating the feeder cell layer, and changing the presence or concentrations of fetal bovine serum or serum substitutes.

Example 7

Maintenance of a Human Pluripotent ES Cell on a Human HS-5 Feeder Cell Layer

Routine Cell Maintenance: Human embryonic stem cells (HESCs) identified as BGN01 (BresaGen Inc., Athens, Ga.) were used in this work. The HECSs were grown in DMEM/F12 (50/50) supplemented with 15% FCS, 5% knockout serum replacer (Invitrogen), 1× non-essential amino acids (Invitrogen), L-Glutamine (20 mM), penicillin (0.5 U/ml), streptomycin (0.5 U/ml), human LIF (10 ng/ml, Chemicon) and FGF-2 (4 ng/ml, Sigma). The human ES cells were grown on feeder layers of mouse primary embryonic fibroblasts that were mitotically inactivated by treatment with mitomycin-C. Feeder cells were re-plated at $1.2 \times 10^6$ cells per 35 mm dish. The mitotically inactivated fibroblasts were cultured for at least 2 days prior to the plating of HESCs. The HESCS were manually passaged onto fresh fibroblast feeder layers every 3-4 days using a fire-pulled and flame polished Pasteur pipette. Briefly, the barrel of the Pasteur pipette was melted in a small gas flame and drawn out to a bore of about 100 μm, broken off perpendicular to the length of the pipette, and then the tip was briefly touched to the flame in order to smooth any sharp edges.

Using this pipette controlled by a mouth tube, regions of colonies of undifferentiated morphology were broken into pieces approximately 10-20 cells across. These pieces were collected and 20 to 50 were transferred to fresh plates that were coated with feeder layers of mitotically inactivated mouse primary embryonic fibroblasts.

Isolation of human feeder cells: Human bone marrow stromal cells, HS-5 cells, (ATCC Accession number CRL-11882) were purchased from a commercial source. HS-5 cells are known to express granulocyte colony-stimulating factor (G-CSF); granulocyte-macrophage-CSF (GM-CSF); macrophage-CSF (M-CSF); steel cell factor (SCF); macrophage-inhibitory protein-1 alpha; IL-1 alpha; IL-1beta; IL-1RA; IL-3; IL-6; IL-8; IL-11; and human leukemia inhibitory factor (hLIF). HS-27A cells (ATCC Accession Number CRL-2496) are also used as a human feeder cell.

HS-5 were routinely cultured in 90% Dulbecco's modified Eagle's medium (containing 4 mM L-glutamine, adjusted to contained 1.5 g/L sodium bicarbonate and 4.5 g/L glucose), with 10% fetal bovine serum. The cells were routinely cultured at 37° According to at 10% $CO_2$. A subcultivation ration of 1:3 to 1:9 is recommended.

HS-5 cells are HPV-16 E6/E7 transformed. HS-5 cell lines, because they were transformed, were not capable of being mitotically inactivated by irradiation of Mitomycin C. When the HS-5 cells were inactivated, they died. Therefore, HS-5 cells were necessarily used as actively growing feeder layers. HS-5 cells were plated at a lower density than used for MEFs, typically at $0.5 \times 10^6$-$4 \times 10^6$ cells per 35 mm dish. The growth of the cells was monitored and when the cells were just subconfluent, they were used for feeder layers for HES cells.

Co-culture of human feeder cells and human ES cells: To test the ability of the human feeder cells to support and maintain the proliferation of human ES cells, undifferentiated pieces of HESC colonies were collected as described and transferred to the HS-5 feeder cell layer. Generally, clumps of HESCs that were transferred to the HS-5 feeder cell layer usually consisted of 10-1000 cells, where the typical number of cells per clump was approximately 100. 5-50 clumps were plated on the cell monolayer, where the typical number of clumps plated is around 20. The human ES cells were visually inspected to ensure that they attach to the monolayer of human feeder cells. After 3 to 6 days on the new feeder layers, regions of colonies with the morphology characteristic of undifferentiated cells were collected as before and passaged again onto the same cell type. This procedure was done repeatedly, up to 5 times.

Immunostaining: At occasional passages, samples of the HESCs were taken and plated overnight onto permanox slides with a MEF feeder layer for immunostaining to demonstrate expression of markers characteristic of pluripotent cells.

The cells were rinsed with 1×PBS and fixed in 4% paraformaldehyde, 4% sucrose in 1×PBS for 30 minutes at room temperature. The cells were then washed in 1× PBS and stored at 4° C. To perform immunostaining, the cells were washed in blocking buffer (3% goat serum, 1% polyvinyl Pyrolidone, 0.3% Triton X-100 in wash buffer) for one hour at room temperature, and then incubated with the appropriate dilution of the primary antibody, or combination of antibodies for 4-6 hours at room temperature. The primary antibodies were: anti-SSEA-1, a mouse monoclonal antibody (Developmental Studies Hybridoma Bank, MC-480) at a ⅕ dilution; anti-SSEA-3, a mouse monoclonal antibody (Developmental Studies Hybridoma Bank, MC-631) at a ⅕ dilution; anti-SSEA-4, a mouse monoclonal antibody (Developmental Studies Hybridoma Bank, MC-813-70) at a ⅕ dilution; Tra 1-60 (ATCC HB-4783) at a dilution of 1/10 ; Tra 1-81 (ATCC HB-4784) at a dilution of 1/12 ; and anti-OCT4 (Santa Cruz Biotechnology, C-20, cat # SC-8629) at a dilution of 1/200.

The cells were then washed in wash buffer (50 mM Tris-HCL pH 7.5, and 2.5 mM NaCl; 3 times for 5 minutes each). The cells were then incubated for a minimum of 2 hours in secondary antibodies diluted 1:1000, followed by washing in wash buffer. The secondary antibodies were Alexa Fluor 488 (green) or Alexa Fluor 568 (red) conjugated goat anti-chicken, anti-rabbit, or anti-mouse antibodies, all available from Molecular Probes. The cells were stained with 5 ng/ml DAPI to detect cell nuclei, and were then washed from overnight to 2 days in a large volume of wash buffer. The slides were mounted with mounting medium and a cover slip. Slides were visualized using a either a NIKON TS100 inverted microscope or a NIKON TE 2000-S inverted microscope with a Q Imaging digital camera.

Results

Cell culture observations: When cultured with the HS-5 cells, the HES cells initially spread out to form a more translucent layer of cells, maintaining the high nuclear to cytoplasm ratio characteristic of pluripotent ES cells. After four to six days the cells began to mound up on the periphery of each colony, assuming a morphology that resembled the undifferentiated regions of the cells grown under the normal conditions using MEFs as a feeder layer (See FIGS. 1A, and B). Cells from these peripheral regions of the colonies were passaged to fresh feeders of HS-5 cells, and also were sampled for antibody detection of antigens expressed by pluripotent cells. HES cells were passaged 5 times on these cells for a total of 42 days.

Cells with undifferentiated morphology after culture on HS-5 cells express the SSEA-3, SSEA-4 and Tra 1-81 epitopes characteristic of pluripotent ES cells (See FIGS. 2A-J). Significantly, these cells express OCT-4, the transcription factor characteristic of pluripotent cells (See FIG. 2A).

These indicators of pluripotency are consistent with previously reported results for human ES cells (Thomson, 1998 supra), and provide evidence that the human ES cell lines maintained on a human HS-5 feeder cell layer are pluripotent.

Example 8

Maintenance of a Human Pluripotent ES Cell on a Human KEL FIB Feeder Cell Layer

Routine Cell Maintenance: Human embryonic stem cells (HESCs) identified as BGN01 (BresaGen, Inc. Athens, Ga.) were used in this work. The HECSs were grown in DMEM/F12 (50/50) supplemented with 15% FCS, 5% knockout serum replacer (Invitrogen), 1× non-essential amino acids (Invitrogen), L-Glutamine (20 mM), penicillin (0.5 U/ml), streptomycin (0.5 U/ml), human LIF (10 ng/ml, Chemicon) and FGF-2 (4 ng/ml, Sigma). The human ES cells were grown on feeder layers of mouse primary embryonic fibroblasts that were mitotically inactivated by treatment with mitomycin-C. Feeder cells were re-plated at $1.2 \times 10^6$ cells per 35 mm dish. The mitotically inactivated fibroblasts were cultured for at least 2 days prior to the plating of HESCs. The HESCS were manually passaged onto fresh fibroblast feeder layers every 3-4 days using a fire-pulled and flame polished Pasteur pipette. Briefly, the barrel of the Pasteur pipette was melted in a small gas flame and drawn out to a bore of about 0.1 mm, broken off perpendicular to the length of the pipette, and then the tip was briefly touched to the flame in order to smooth any sharp edges.

Using this pipette controlled by a mouth tube, regions of colonies of undifferentiated morphology were broken into pieces approximately 10-20 cells across. These pieces were collected and 20 to 50 were transferred to fresh plates that were coated with feeder layers of mitotically inactivated mouse primary embryonic fibroblasts.

Isolation of human feeder cells: The KEL FIB cell line (ATCC Accession Number CRL-1762), adherent fibroblast like cells derived from keloids, was purchased from a commercial source. Keloids are benign dermal tumors that form during an abnormal wound-healing process in genetically susceptible individuals. Keloids have been shown to express high levels of collagen, hyaluronic acid, fibronectin, and cytokines such as Melanoma Growth Stimulatory Activity Chemokines (MGSA/GRO-alpha), TGF beta isoforms 1, 2 and 3, Cyclooxygenase 1 (COX-1), IL-6, vascular endothelial growth factor (VEGF), POMC-derived peptides such as alpha beta and gamma-MSH and ACTH, PAI-1, and bFGF. IL-6 signals through the gp-130 pathway used by LIF.

KEL FIB cells were routinely propagated in ATCC medium (DMEM with 4.5 g/L glucose and 10% fetal bovine serum), with an atmosphere of 10% $CO_2$ at a temperature of 37° C. To subculture the cells, the medium was removed, the monolayer was rinsed with fresh 0.25% trypsin, 0.02% EDTA solution. The trypsin was removed and the culture was allowed to remain at room temperature of 37° C. until the cells detached (5-10 minutes). Fresh medium was then added, and the cells were aspirated and dispensed into new flasks. A subcultivation ration of 1:2 to 1:4 is recommended. The medium is renewed 2-3 times per week.

These cells were plated at a density that gave a confluent monolayer, and were treated with mitomycin C (10 ug/ml) for one hour. The number of cells that gave a confluent monolayer varied from cell type, but for the KEL FIB cells this was found to be in the range of 0.5 to 1.5 million cells per 35 mm petri dish. Alternatively, the feeder cell layer could be mitotically inactivated using irradiation. In addition, KEL FIB cells which had not been inactivated mitotically were also shown to support the proliferation of undifferentiated HES cells.

Co-culture of human feeder cells and human ES cells: To test the ability of the human feeder cells to support and maintain the proliferation of human ES cells, undifferentiated pieces of HESC colonies were collected as described and transferred to the KEL FIB feeder cell layer. Generally, clumps of HESCs that were transferred to the KEL FIB feeder cell layer usually consisted of 10-1000 cells, where the typical number of cells per clump was approximately 100. 5-50 clumps were plated on the cell monolayer, where the typical number of clumps plated is around 20. The human ES cells were visually inspected to ensure that they attach to the monolayer of human feeder cells. After 3 to 6 days on the new feeder layers, regions of colonies with the morphology characteristic of undifferentiated cells were collected as before and passaged again onto the same cell type. Cells were passaged on the KEL FIB cells for 3 passages, over a total of 15 days Immunostaining: At occasional passages, samples of the HESCs were taken and plated onto permanox slides for immunostaining to demonstrate expression of markers characteristic of pluripotent cells.

The cells were rinsed with 1×PBS and fixed in 4% paraformaldehyde, 4% sucrose in 1×PBS for 30 minutes at room temperature. The cells were then washed in 1× PBS and stored at 4° C. To perform immunostaining, the cells were washed in blocking buffer (3% goat serum, 1% polyvinyl Pyrolidone, 0.3% Triton X-100 in wash buffer) for one hour at room temperature, and then incubated with the appropriate dilution of the primary antibody, or combination of antibodies for 4-6 hours at room temperature. The primary antibodies were: anti-SSEA-1, a mouse monoclonal antibody (Developmental Studies Hybridoma Bank, MC-480) at a ⅕ dilution; anti-SSEA-3, a mouse monoclonal antibody (Developmental Studies Hybridoma Bank, MC-631) at a ⅕ dilution; anti-SSEA-4, a mouse monoclonal antibody (Developmental Studies Hybridoma Bank, MC-813-70) at a ⅕ dilution; Tra 1-60 (ATCC HB-4783) at a dilution of 1/10 ; Tra 1-81 (ATCC HB-4784) at a dilution of 1/12 ; and anti-OCT4 (Santa Cruz Biotechnology, C-20, cat # SC-8629) at a dilution of 1/200.

The cells were then washed in wash buffer (50 mM Tris-HCL pH 7.5, and 2.5 mM NaCl; 3 times for 5 minutes each). The cells were then incubated for a minimum of 2 hours in secondary antibodies diluted 1:1000, followed by washing in wash buffer. The secondary antibodies were Alexa Fluor 488 (green) or Alexa Fluor 568 (red) conjugated goat anti-chicken, anti-rabbit, or anti-mouse antibodies, all available from Molecular Probes. The cells were stained with 5 ng/ml DAPI to detect cell nuclei, and were then washed from overnight to 2 days in a large volume of wash buffer. The slides were mounted with mounting medium and a cover slip. Slides were visualized using a either a NIKON TS100 inverted microscope or a NIKON TE 2000-S inverted microscope with a Q Imaging digital camera.

Results

Figure 3:
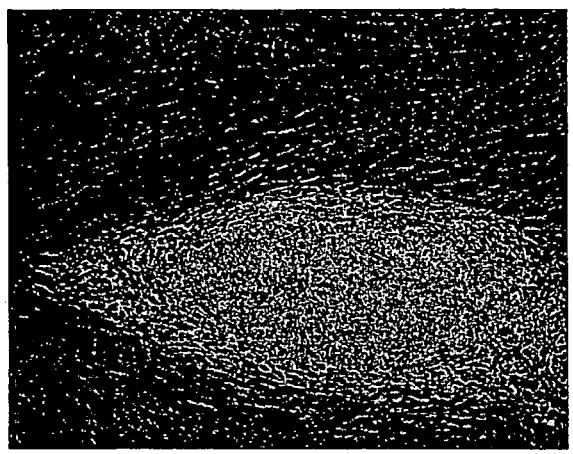
FIGS. 3A, B, C, and D show unstained phase-contrast images of colonies of BGN01 human embryonic stem cells grown on KEL FIB feeder cells for 3 days (A and B) and 4 days (C and D) after culture. The colonies have similar appearance to those grown on mouse embryonic fibroblast feeder layers, and retain the compact cell morphology with high nuclear to cytoplasm ratio characteristic of pluripotent ES cells.
Figure 3:
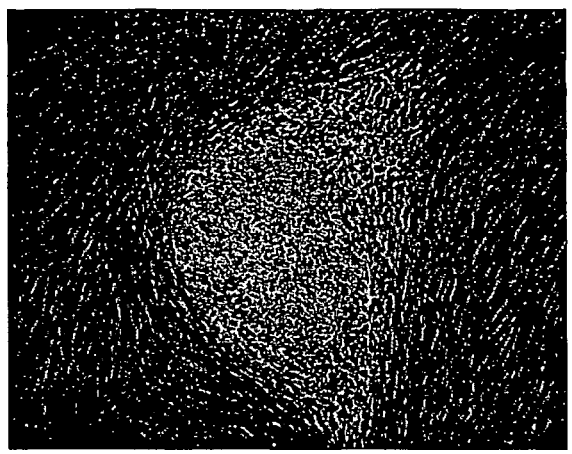
Figure 3:
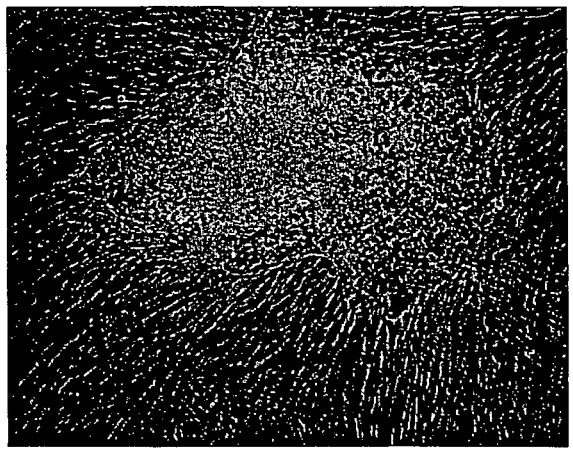
Figure 3:
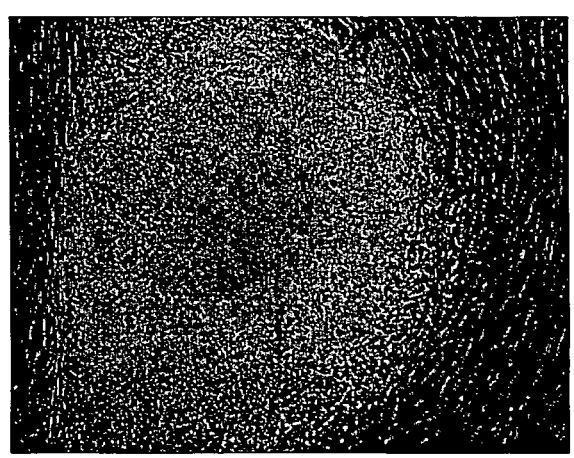

Cell culture observations: When grown on KEL FIB feeder cell layers, the morphology of the HES cells was almost identical to that morphology observed when the HES cells were grown on the MEF feeder layers (See FIG. 3). The cells had the high nuclear to cytoplasm ratio, and the boundaries were distinct and light refractile. The pieces of colony passaged did not spread out initially as they did on the HS-5 cells. As the colony grew, the KEL FIB cells seemed to line up and to push against the colony to give it more angular aspects to the edge.

Figure 4:
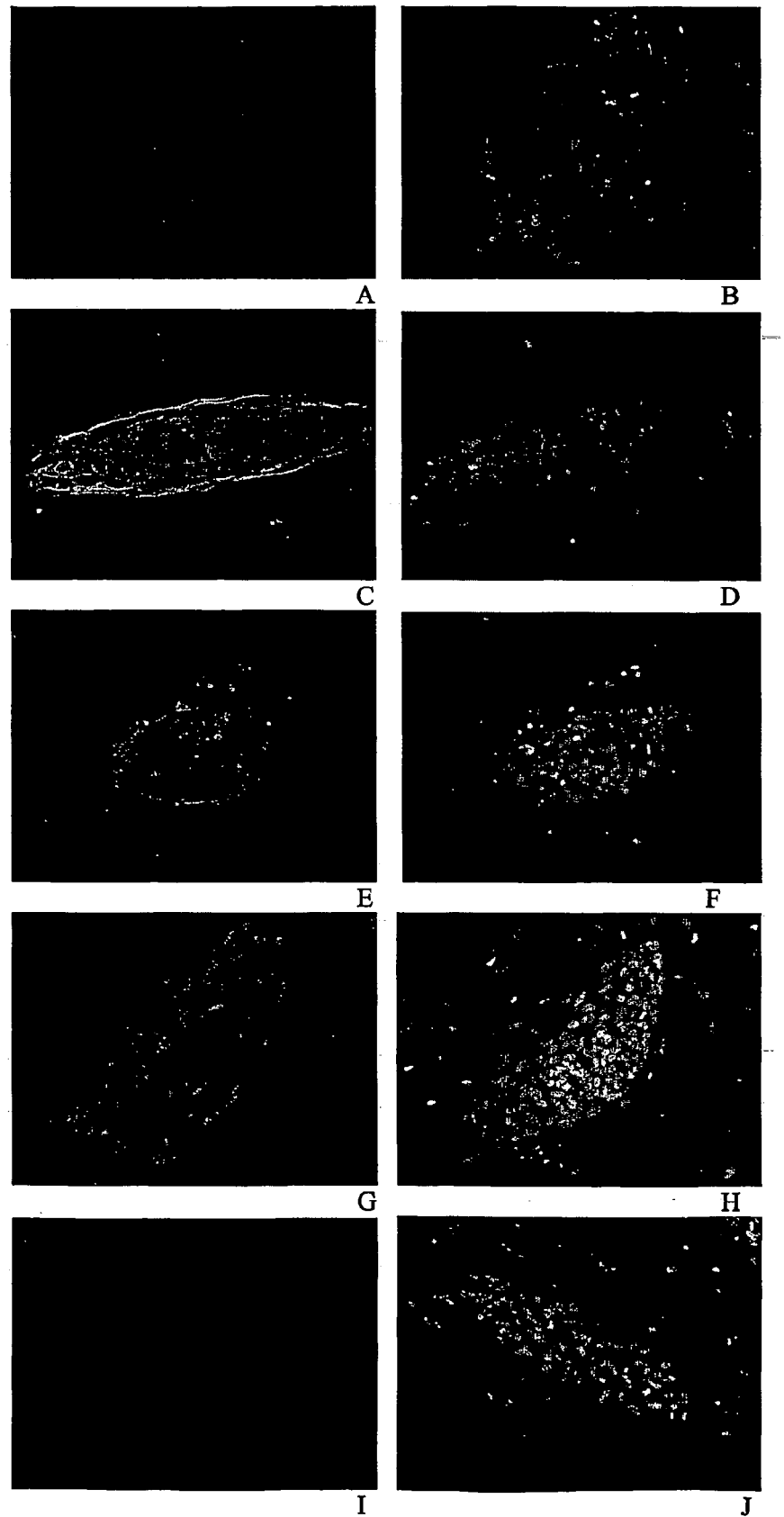
FIGS. 4A-J show the immunostaining of BGN01 human embryonic stem cells grown on KEL FIB feeder cells. For each marker, the same cells were counterstained with the nuclear stain, DAPI. The cells stain positively for OCT-4 (FIG. 4A), Tra-1-60 (FIG. 4C), SSEA-3 (FIG. 4E), and SSEA4, (FIG. 4H). The cells are negative for SSEA1 (FIG. 4J). The colonies therefore express all of the markers for pluripotency. Note that the feeder cells, which can be visualized after DAPI staining, are not immunoreactive with any of the antibodies.

Cells that had been maintained on KEL fib cells for 15 days, and three passages maintained the morphology of pluripotent cells. After 2 passages and 10 days, cells with undifferentiated morphology after culture on KEL FIB cells were immunostained to test for markers characteristic of pluripotent cells (FIGS. 4A, C, E, G, and I). For each marker, the same cells were counterstained with the nuclear stain DAPI (FIGS. 4B, D, F, H, and J). The cells express OCT-4, the transcription factor characteristic of pluripotent cells (FIG. 4A), Tra-1-60 (FIG. 4C), SSEA-3 (FIG. 4E), and SSEA-4 (FIG. 4H). However, these cells do not express the SSEA-1 epitope, an epitope that is expressed in differentiating HES cells (FIG. 4J).

These indicators of pluripotency are consistent with previously reported results for human ES cells (Thomson, 1998 supra), and provide evidence that the human ES cell lines maintained on a human KEL FIB feeder cell layer are pluripotent.

Example 9

Maintenance of a Human Pluripotent ES Cell on a Human Fallopian Ductal Epithelial Feeder Cell Layer Except as outlined below, all of the materials and methods are described in Examples 1-8.

Isolation of human feeder cells: Human Fallopian ductal epithelial feeder cells are obtained from commercial sources, or are obtained through biopsies of human tissues. In certain embodiments the Fallopian ductal epithelial cell is fetal, or neonatal. In other embodiments the Fallopian ductal epithelial cell is obtained from an adult. In one embodiment the Fallopian ductal epithelial cell is a cell line. In another embodiment, the human Fallopian ductal epithelial cell is a primary cell, wherein the primary cell is obtained from a biopsy. Further, human feeder cell can be mitotically inactivated prior to culturing the stem cell with the feeder cell layer.

Primary Fallopian ductal epithelial cell lines are established from biopsies of human Fallopian tubes. Generally, the biopsy tissue is dissociated using chemical means (i.e. trypsin, chymotrypsin, etc.) and physical means (i.e. passage through a narrow bore pipette). The cells can be further dissociated into a single cell suspension by a treatment with trypsin-EDTA. After dissociation, the primary cells are washed and plated on tissue culture dishes. The Fallopian ductal epithelial cells are generally cultured at 37° C. and 5% $CO_2$.

The human feeder cells are cultured in HES medium, which is altered to optimize the growth of each feeder cell. Alternatively, the Fallopian ductal epithelial cells are cultured in a medium optimized for the growth of Fallopian ductal epithelial cells. When the feeder cell is subconfluent or reaches confluence, the monolayer is used as a cell feeder layer for the culture of the human stem cell.

Co-culture of human feeder cells and human ES cells: To test the ability of the human feeder cells to support and maintain the human ES cell, the isolated human ES cell line is collected from its standard growth conditions on MEFs, as described in Example 1. Clumps of human ES cells are re-plated onto the human feeder cell monolayer. The clumps usually consist of 10-1000 cells, where the typical number of cells per clump is approximately 100. 5-50 clumps are plated on the cell monolayer, where the typical number of clumps plated is around 20. The human ES cells are visually inspected to ensure that they attach to the monolayer of human feeder cells.

The human ES cell line co-cultured with the human Fallopian ductal epithelial cell layer is characterized to ensure pluripotency using tests well known in the art. For example, alkaline phosphatase expression is determined. Other indicators of pluripotency are also investigated. These include, but are not limited to, karyotype analysis; the presence of stage specific embryonic antigens such as SSEA-1 (Solter, D. and B. Knowles, Proc. Natl. Acad. Sci. USA 75: 5565-5569, 1978), SSEA-3, SSEA-4 (Kannagi, R., et al, Embo J. 2:2355-2361, 1983) and epitopes recognized by the antibodies TRA-1-60 (ATCC HB-4783) and TRA-1-81 (ATCC HB-4784) (Andrews, P., et al., 1984 supra); in vitro differentiation into cell types from all three germ cell layers; DBHB antibody data; and the ability of these cells to form teratocarcinomas or teratomas when injected into immuno-compromised (SCID) mice. The other indicators of pluripotency are consistent with previously reported results for human ES cells (Thomson, 1998 supra), and provide evidence that the human ES cell lines maintained on a human Fallopian ductal epithelial cell feeder layer are pluripotent.

The culture conditions for the co-culture of human Fallopian ductal epithelial cells with human ES cells are optimized to maintain human ES cells in a pluripotent state for indefinite periods of time (e.g. greater than 1 year). The culture conditions are optimized by changing the culture medium, varying the temperature, varying the concentrations of the human ES cell or the feeder cell, adding different supplemental growth factors, mitotically inactivating the feeder cell layer, and changing the presence or concentrations of fetal bovine serum or serum substitutes.

Example 10

Maintenance of a Human Pluripotent ES Cell on a Human Fetal Skin Fibroblast Feeder Cell Layer Except as outlined below, all of the materials and methods are described in Examples 1-9.

Isolation of human feeder cells: Human fetal skin fibroblast feeder cells are obtained from commercial sources, or are obtained through biopsies of human tissues. In certain embodiments the Fallopian ductal epithelial cell is fetal, or neonatal. In one embodiment the fetal skin fibroblast cell is a cell line. In another embodiment, the human fetal skin fibroblast cell is a primary cell, wherein the primary cell is obtained from a biopsy. Further, human feeder cell can be mitotically inactivated prior to culturing the stem cell with the feeder cell layer.

Primary fetal skin fibroblast cell lines are established from biopsies of human skin. Generally, the biopsy tissue is dissociated using chemical means (i.e. trypsin, chymotrypsin, etc.) and physical means (i.e. passage through a narrow bore pipette). The cells can be further dissociated into a single cell suspension by a treatment with trypsin-EDTA. After dissociation, the primary cells are washed and plated on tissue culture dishes. Alternatively, the fetal skin fibroblast biopsies are not dissociated into a single cell suspension. The fetal skin fibroblast cells are generally cultured at 37° C. and 5% $CO_2$.

The human feeder cells are cultured in HES medium, which is altered to optimize the growth of each feeder cell. Alternatively, the fetal skin fibroblast cells are cultured in a medium optimized for the growth of fetal skin fibroblast cells. When the feeder cell is subconfluent or reaches confluence, the monolayer is used as a cell feeder layer for the culture of the human stem cell.

Co-culture of human feeder cells and human ES cells: To test the ability of the human feeder cells to support and maintain the human ES cell, the isolated human ES cell line is collected from its standard growth conditions on MEFs, as described in Example 1. Clumps of human ES cells are re-plated onto the human feeder cell monolayer. The clumps usually consist of 10-1000 cells, where the typical number of cells per clump is approximately 100. 5-50 clumps are plated on the cell monolayer, where the typical number of clumps plated is around 20. The human ES cells are visually inspected to ensure that they attach to the monolayer of human feeder cells.

The human ES cell line co-cultured with the human fetal skin fibroblast cell layer is characterized to ensure pluripotency using tests well known in the art. For example, alkaline phosphatase expression is determined. Other indicators of pluripotency are also investigated. These include, but are not limited to, karyotype analysis; the presence of stage specific embryonic antigens such as SSEA-1 (Solter, D. and B. Knowles, Proc. Natl. Acad. Sci. USA 75: 5565-5569, 1978), SSEA-3, SSEA-4 (Kannagi, R., et al, Embo J. 2:2355-2361, 1983) and epitopes recognized by the antibodies TRA-1-60 (ATCC HB-4783) and TRA-1-81 (ATCC HB-4784) (Andrews, P., et al., 1984 supra); in vitro differentiation into cell types from all three germ cell layers; DBHB antibody data; and the ability of these cells to form teratocarcinomas or teratomas when injected into immuno-compromised (SCID) mice. The other indicators of pluripotency are consistent with previously reported results for human ES cells (Thomson, 1998 supra), and provide evidence that the human ES cell lines maintained on a human fetal skin fibroblast cell feeder layer are pluripotent.

The culture conditions for the co-culture of human fetal skin fibroblast cells with human ES cells are optimized to maintain human ES cells in a pluripotent state for indefinite periods of time (e.g. greater than 1 year). The culture conditions are optimized by changing the culture medium, varying the temperature, varying the concentrations of the human ES cell or the feeder cell, adding different supplemental growth factors, mitotically inactivating the feeder cell layer, and changing the presence or concentrations of fetal bovine serum or serum substitutes.

Example 11

Maintenance of a Human Pluripotent ES Cell on a Human Feeder Cell Layer

Isolation of human feeder cells: Human feeder cells are obtained from commercial sources, or are obtained through biopsies of human tissues. Preferred human feeder cell types include the group consisting of a human fibroblast cell, a MRC-5 cell, a human embryonic kidney cell, a mesenchymal cell, an osteosarcoma cell, a keratinocyte, a chondrocyte, a Fallopian ductal epithelial cell, a liver cell, a cardiac cell, a bone marrow stromal cell, a granulosa cell, a skeletal muscle cell, and an aortic endothelial cell. Preferred commercially available cell lines include cell lines selected from the group consisting of a human fibroblast cell, a MRC-5 cell, a human embryonic kidney cell, a mesenchymal cell, an osteosarcoma cell, a keratinocyte, a chondrocyte, a Fallopian ductal epithelial cell, and a liver cell. In preferred embodiments, the MRC-5 cell, a diploid lung cell line, has ATCC Catalog Number 55-X; the human embryonic kidney cell has ATCC Accession Number CRL 1573.1; the human keratinocyte is retrovirally transformed and has ATCC Accession Number CRL-2309; the human osteosarcoma cell has ATCC Accession Number HTB-96; and the mesenchymal cell is a human fetal palatal mesenchymal cell with ATCC Accession Number CRL-1486. In another embodiment, the human feeder cell is a primary cell, wherein the primary cell is obtained from a biopsy and is selected from the group consisting of a cardiac cell, a mesenchymal cell, a keratinocyte, a bone marrow stromal cell, a chondrocyte, a granulosa cell, a Fallopian ductal epithelial cell, an osteosarcoma cell, and a liver cell. In another embodiment, the human feeder cell is a an aortic endothelial cell. Further, human feeder cell can be mitotically inactivated prior to culturing the stem cell with the feeder cell layer.

Primary cell lines are established from biopsies of human tumors, or other tissues. Generally, the biopsy is dissociated using chemical means (i.e. trypsin, chymotrypsin, etc.) and physical means (i.e. passage through a narrow bore pipette). The cells can be further dissociated into a single cell suspension by a treatment with trypsin-EDTA. After dissociation, the primary cells are washed with HES cell medium and plated on tissue culture dishes. The human feeder cells are generally cultured at 37° C. and 5% $CO_2$.

The human feeder cells are cultured in HES medium, which is altered to optimize the growth of each feeder cell. When the feeder cell reaches confluence, the monolayer is used as a cell feeder layer for the culture of the human stem cell.

Co-culture of human feeder cells and human ES cells: To test the ability of the human feeder cells to support and maintain the human ES cell, the isolated human ES cell line is collected from its standard growth conditions on MEFs, as described in Example 1. Clumps of human ES cells are re-plated onto the human feeder cell monolayer. The clumps usually consist of 10-1000 cells, where the typical number of cells per clump is approximately 100. 5-50 clumps are plated on the cell monolayer, where the typical number of clumps plated is around 20. The human ES cells are visually inspected to ensure that they attach to the monolayer of human feeder cells.

The human ES cell line co-cultured with the human feeder cell layer is characterized to ensure pluripotency using tests well known in the art. For example, alkaline phosphatase expression is determined. Other indicators of pluripotency are also investigated. These include, but are not limited to, karyotype analysis; the presence of stage specific embryonic antigens such as SSEA-1 (Solter, D. and B. Knowles, Proc. Natl. Acad. Sci. USA 75: 5565-5569, 1978), SSEA-3, SSEA-4 (Kannagi, R., et al, Embo J. 2:2355-2361, 1983) and epitopes recognized by the antibodies TRA-1-60 (ATCC HB-4783) and TRA-1-81 (ATCC HB-4784) (Andrews, P., et al., 1984 supra); in vitro differentiation into cell types from all three germ cell layers; DBHB antibody data; and the ability of these cells to form teratocarcinomas or teratomas when injected into immuno-compromised (SCID) mice. The other indicators of pluripotency are consistent with previously reported results for human ES cells (Thomson, 1998 supra), and provide evidence that the human ES cell lines maintained on a human cell feeder layer are pluripotent.

The culture conditions for the co-culture of different human feeder cells with human ES cells are optimized to maintain human ES cells in a pluripotent state for indefinite periods of time (e.g. greater than 1 year). The culture conditions are optimized by changing the culture medium, varying the temperature, varying the concentrations of the human ES cell or the feeder cell, adding different supplemental growth factors, mitotically inactivating the feeder cell layer, and changing the presence or concentrations of fetal bovine serum or serum substitutes.

Example 12

Isolation and Maintenance of a Human Pluripotent ES Cell on a Human Feeder Cell Layer Except as outlined below, all of the materials and methods are described in Examples 1-11.

Human embryos are obtained as described in Example 1. The ICM of the embryo is isolated using the technique described in Example 1, or using other techniques that are well known in the art. The ICM is plated onto and allowed to attach to a human feeder cell layer. The human feeder cell layer is generated as described in Example 6. After 7-30 days, ICM-derived masses are isolated and dissociated as described in Example 1. The dissociated cells are re-plated on a fresh human feeder cell layer. Colonies of cells with the morphology characteristic of human pluripotent ES cells are isolated and re-plated as described in Example 1, except the cells are plated on a human feeder cell layer. The resulting ES cells are routinely passaged using techniques well known in the art. The human feeder cell at each stage of the above procedure is preferably selected from the group described in Example 11, however, the same or different human feeder cells can be used for each stage of the described procedure.

The human ES cell line co-cultured with the human feeder cell layer is characterized to ensure pluripotency using tests well known in the art. For example, alkaline phosphatase expression is determined. Other indicators of pluripotency are also investigated. These include, but are not limited to, karyotype analysis; the presence of stage specific embryonic antigens such as SSEA-1 (Solter, D. and B. Knowles, Proc. Natl. Acad. Sci. USA 75: 5565-5569, 1978), SSEA-3, SSEA-4 (Kannagi, R., et al., Embo J. 2:2355-2361, 1983) and epitopes recognized by the antibodies TRA-1-60 (ATCC HB-4783) and TRA-1-81 (ATCC HB-4784) (Andrews, P., et al., Hybridoma 3:347-361, 1984); in vitro differentiation into cell types from all three germ cell layers; DBHB antibody data; and the ability of these cells to form teratocarcinomas or teratomas when injected into immuno-compromised (SCID) mice. The other indicators of pluripotency are consistent with previously reported results, and provide evidence that the human ES cell lines isolated and maintained on human feeder cell layers are pluripotent.

The conditions for the isolation and maintenance of a human ES cell on a human feeder cell layer are optimized so to maintain human ES cells in a pluripotent state for indefinite periods of time (e.g. greater than 1 year). The culture conditions are optimized by changing the culture medium, varying the temperature, varying the concentrations of the human ES cell or the feeder cell, adding different supplemental growth factors, mitotically inactivating the feeder cell layer, and changing the presence or concentrations of fetal bovine serum or serum substitutes.

Example 13

Maintenance of a Human Pluripotent ES Cell on a Human Cell Factor Conditioned Medium Except as outlined below, all of the materials and methods are described in Examples 1-12.

Human embryos are obtained as described in Example 1, and human pluripotent ES cells are obtained as described in any of Examples 1-12. The dissociated ICM-derived cells are re-plated without a feeder cell layer, in the presence of conditioned medium.

The conditioned medium is obtained from a human feeder cell. The human feeder cell is generated as described in Example 11. The conditioned medium is collected from confluent human feeder cell culture. The human feeder cell may be a primary cell, a commercially available cell, and/or an immortalized cell. In one embodiment, the human feeder cell is mitotically inactivated prior to the collection of the medium. The human feeder cells and cell-debris are removed from the culture medium, where the removal is typically by centrifugation or filtration. The human feeder cell releases a soluble cell factor into the conditioned medium that is not removed by the centrifugation or filtration process. The conditioned medium is useful in promoting the growth of an ES cell, maintaining the survival of the ES cell in a pluripotent state, stimulating the differentiation of a human embryonic stem cell, and/or stimulating reversal of the differentiation of a cell. In a preferred embodiment the conditioned medium is obtained from a bone marrow stromal cell, a skin keloid fibroblast, or a skeletal muscle cell.

The conditioned medium is added to the human ES cells in an amount that is empirically determined to maintain the ES cell in the desired pluripotent or selectively differentiated state. The state of the human ES cell is determined using tests and markers well known in the art, and described herein.

We claim:

1. A human pluripotent stem cell culture, comprising a human embryonic stem cell and a human feeder cell, wherein the human feeder cell is selected from the group consisting of a fetal skin fibroblast cell and a skin keloid fibroblast cell, and wherein the human feeder cell maintains the human embryonic stem cell in an undifferentiated state for at least two passages.

2. The human pluripotent embryonic stem cells culture of claim 1, where the human feeder cell is a skin keloid fibroblast cell.

3. The human embryonic stem cell culture of claim 1, wherein the skin keloid fibroblast cell is ATCC deposit number CRL-1762.

4. The human pluripotent embryonic stem cells culture of claim 1, where the human feeder cell is a fetal skin fibroblast cell.

5. A method of maintaining a human embryonic stem cell culture in an undifferentiated state for at least two passages, comprising culturing a human embryonic stem cell on a human feeder cell layer, wherein the human feeder cell is selected from the group consisting of a fetal skin fibroblast cell and a skin keloid fibroblast cell.

6. The method of claim 5, wherein the human feeder cell is a skin keloid fibroblast cell.

7. The method of claim 6, wherein the skin keloid fibroblast cell is ATCC deposit number CRL-1762.

8. The human pluripotent embryonic stem cells culture of claim 5, where the human feeder cell is a fetal skin fibroblast cell.

9. A method of maintaining a human embryonic stem cell culture, comprising the steps of:
    (a) isolating cells from the inner cell mass of a blastocyst;
    (b) plating the inner cell mass cells, wherein inner cell mass-derived cell masses are formed; and
    (c) re-plating and maintaining the human embryonic stem cell colony on a human feeder cell layer, wherein the human feeder cell is selected from the group consisting of a fetal skin fibroblast cell and a skin keloid fibroblast cell, thereby maintaining a human embryonic stem cell in an undifferentiated state for at least two passages.

10. The method of claim 9, further comprising the step of selecting a colony with the characteristics of a human embryonic stem cell after re-plating the inner cell mass cells and before re-plating the human embryonic stem cell colony.

11. A method of isolating and maintaining a human embryonic stem cell culture, comprising the steps of:
    (a) isolating cells from the inner cell mass of a blastocyst;
    (b) plating the inner cell mass cells on a human feeder cell, wherein the human feeder cell is selected from the group consisting of a fetal skin fibroblast cell and a skin keloid fibroblast cell, and wherein inner cell mass-derived cell masses are formed; and
    (c) re-plating and maintaining the human embryonic stem cell colony on a human feeder cell to thereby isolate and maintain a human pluripotent embryonic stem cell in an undifferentiated state for at least two passages.

12. The method of claim 11, wherein the inner cell mass-derived cells are dissociated into clusters, and re-plated on a human feeder cell, and a colony is selected with the characteristics of a human embryonic stem cell prior to re-plating the selected human embryonic stem cell colony on a human feeder cell.

13. A human pluripotent stem cell culture, comprising a human embryonic stem cell in a media comprising bFGF and a human feeder cell, wherein the human feeder cell is a bone marrow stromal cell, and wherein the human feeder cell maintains the human embryonic stem cell in an undifferentiated state for at least two passages.

14. The human pluripotent embryonic stem cell culture of claim 13, wherein the bone marrow stromal cell is ATCC deposit number CRL-11882.

15. A method of maintaining a human embryonic stem cell culture in an undifferentiated state for at least two passages, comprising culturing a human embryonic stem cell in a media comprising bFGF and on a human feeder cell layer, wherein the human feeder cell is a bone marrow stromal cell.

16. The method of claim 15, wherein the bone marrow stromal cell is ATCC deposit number CRL-11882.

17. A method of maintaining a human embryonic stem cell culture, comprising the steps of:
    (a) isolating cells from the inner cell mass of a blastocyst;
    (b) plating the inner cell mass cells in a media comprising bFGF, wherein inner cell mass-derived cell masses are formed; and
    (c) re-plating in a media comprising bFGF and maintaining the human embryonic stem cell colony on a human feeder cell layer, wherein the human feeder cell is a bone marrow stromal cell, thereby maintaining a human embryonic stem cell in an undifferentiated state for at least two passages.

18. The method of claim 17, further comprising the step of selecting a colony with the characteristics of a human embryonic stem cell after re-plating the inner cell mass cells and before re-plating the human embryonic stem cell colony.

19. A method of isolating and maintaining a human embryonic stem cell culture, comprising the steps of:
    (a) isolating cells from the inner cell mass of a blastocyst;
    (b) plating the inner cell mass cells in a media comprising bEGE and on a human feeder cell, wherein the human feeder cell is a bone marrow stromal cell, and wherein inner cell mass-derived cell masses are formed; and
    (c) re-plating in a media comprising bFGF and maintaining the human embryonic stem cell colony on a human feeder cell to thereby isolate and maintain a human pluripotent embryonic stem cell in an undifferentiated state for at least two passages.

20. The method of claim 19, wherein the inner cell mass-derived cells are dissociated into clusters, and re-plated on a human feeder cell, and a colony is selected with the characteristics of a human embryonic stem cell prior to re-plating the selected human embryonic stem cell colony on a human feeder cell.

21. The method of claim 20, wherein the inner cell mass-derived cells are dissociated into clusters, and re-plated on a human feeder cell, and a colony is selected with the characteristics of a human embryonic stem cell prior to re-plating the selected human embryonic stem cell colony on a human feeder cell.

* * * * *

UNITED STATES PATENT AND TRADEMARK OFFICE
CERTIFICATE OF CORRECTION

PATENT NO. : 7,432,104 B2
APPLICATION NO. : 10/486408
DATED : October 7, 2008
INVENTOR(S) : Maisam Mitalipova and Ian Lyons It is certified that error appears in the above-identified patent and that said Letters Patent is hereby corrected as shown below:

On the title page, (73) Assignee, delete "BresGen" and insert --BresaGen--.

On the title page, Item (56) insert under "Other Publications", the following:

--AMIT, et al., 2000 "Clonally Derived Human Embryonic Stem Cell Lines Maintain Pluripotency and Proliferative Potential for Prolonged Periods of Culture," *Developmental Biology*, 227:271-278.

BONGSO, et al., 1994 "Isolation and Culture of Inner Cell Mass Cells from Human Blastocysts," *Human Reproduction*, 9:2100-2117.

ODORICO, et al., 2001 "Multilineage Differentiation from Human Embryonic Stem Cell Lines," *Stem Cells*, 19:193-204.

PERA, et al., 2000 "Human Embryonic Stem Cells", *J. Cell Science*, 113:5-10.

REUBINOFF et al., 2000 "Embryonic Stem Cell Lines from Human Blastocysts: Somatic Differentiation *In Vitro*," *Nature Biotechnology*, 18:339-404; Research Errata Nature Biotech., 18:559.

SCHULDINER et al., 2000 "Effects of Eight Growth Factors on the Differentiation of Cells Derived from Human Embryonic Stem Cells," PNAS USA 97:11307-11312.

SHAMBLOTT, et al., 1998 "Derivation of Pluripotent Stem Cells from Cultured Human Primordial Germ Cells," *Proc. Natl. Acad. Sci. USA*, 95:13726-13731.

THOMSON, et al., 1998 "Embryonic Stem Cell Lines Derived from Human Blastocysts," *Science*, 282:1145-1147.

VASIL'EVA and VASIL'EV, 1995 "Effect of the Developmental Stage and Cultivation Conditions of Cow and Mouse Embryos on Preparation of ES-Like Cells," Russian J. Dev. Biol, 26:167-72, Translated from Ontogenez, 26:206-12, 1995.

UNITED STATES PATENT AND TRADEMARK OFFICE
CERTIFICATE OF CORRECTION

PATENT NO. : 7,432,104 B2
APPLICATION NO. : 10/486408
DATED : October 7, 2008
INVENTOR(S) : Maisam Mitalipova and Ian Lyons It is certified that error appears in the above-identified patent and that said Letters Patent is hereby corrected as shown below:

VASIL'EV and VASIL'EVA, 1995 "Factors Influencing the Isolation of Embryonic Stem Cells of Pigs," Russian J. Dev. Biol., 26:163-66, Translated from Ontogenez, 26:201-205, 1995.

XU et al., "Growth of Undiffrentiated Human Embryonic Stem Cells on Defined Matrices with Conditioned Medium," Keystone Symposia Abstract Book, Pluripotent Stem Cells: Biology and Applications, February 2001, A. 133.

WAELTI, et al., 1992 "Co-Culture of Human Keratinocytes on Post-Mitotic Human Dermal Fibroblast Feeder Cells: Production of Large Amounts of Interleukin 6," *Journal of Investigative Dermatology*, 98:805-808.--.

On the title page, under Item (57) Abstract, delete "21 Claims" and insert --20 Claims--.

At column 42, line 40, delete "bEGE" and insert --bFGF--.

At column 42, line 54, delete Claim 21 in its entirety.

Signed and Sealed this

Second Day of December, 2008

JON W. DUDAS
*Director of the United States Patent and Trademark Office*

UNITED STATES PATENT AND TRADEMARK OFFICE
CERTIFICATE OF CORRECTION

PATENT NO.         : 7,432,104 B2                                                         Page 1 of 2
APPLICATION NO. : 10/486408
DATED              : October 7, 2008
INVENTOR(S)        : Maisam Mitalipova et al.

It is certified that error appears in the above-identified patent and that said Letters Patent is hereby corrected as shown below:

At column 41, line 9, delete "embryonic" after "pluripotent".

At column 41, line 9, delete "cells" and insert --cell--.

At column 41, line 12, delete "embryonic" after "human" and insert --pluripotent--.

At column 41, line 15, delete "embryonic" after "pluripotent".

At column 41, line 15, delete "cells" and insert --cell--.

At column 41, line 28, delete "human pluripotent stem cells culture" and insert --method--.

At column 41, line 35, delete "masses" after "cell" and insert --colonies--.

At column 41, line 36, insert --inner cell mass-derived cell colonies-- after "the" and delete "human embryonic stem cell colony".

At column 41, line 40, insert --culture-- after "stem cell".

At column 41, line 43, insert --inner cell mass-derived cell colonies prior to step (c)-- after "selecting" and delete "a colony".

At column 41, line 44, delete "after re-plating the inner cell mass cells and before re-plating the human embryonic stem cell colony".

At column 41, line 49, insert --layer-- after "feeder cell.".

At column 41, line 53, delete "masses" and insert --colonies--.

At column 41, line 54, after "maintaining the" insert --inner cell mass-derived cell colonies on a--.

At column 41, line 55, after "feeder cell" insert --layer--.

At column 41, line 56, after "stem cell" insert --culture--.

At column 41, line 59, delete "cells" and insert --cell colonies--.

At column 41, lines 59-60, delete "and re-plated on a human feederl cell, and a colony is selected" and insert --wherein the cluster--.

CERTIFICATE OF CORRECTION (continued)
U.S. Pat. No. 7,432,104 B2

At column 42, lines 1-3, after "human embryonic stem cell" delete "prior to re-plating the selected human embryonic stem cell colony on a human feeder cell" and insert --is selected prior to step (c)--.

At column 42, line 10, delete "embryonic" after "pluripotent".

At column 42, line 24, after "cell mass-derived cell" delete "masses" and insert --colonies--.

At column 42, line 27, after "the" delete "human embryonic stem" and insert --inner--.

At column 42, line 27, after "cell" delete "colony" and insert --mass-derived cell colonies--.

At column 42, line 30, after "stem cell" insert --culture--.

At column 42, line 33, after "selecting" delete "a colony" and insert --inner cell mass-derived cell colonies--.

At column 42, lines 34-35, after "stem cell" delete "after re-plating the inner cell mass cells and before re-plating the human embryonic stem cell colony" and insert --prior to step (c)--.

At column 42, line 40, after "feeder cell" insert --layer--.

At column 42, line 42, after "cell mass-derived cell" delete "masses" and insert --colonies--.

At column 42, line 44, after "the" insert --inner cell mass-derived cell colonies on a--.

At column 42, line 44, after "human" delete "embryonic stem cell colony on a human".

At column 42, line 45, after "feeder cell" insert --layer--.

At column 42, lines 45-46, after "human" delete "pluripotent".

At column 42, line 46, after "stem cell" insert --culture--.

At column 42, line 49, after "derived" delete "cells" and insert --cell colonies--.

At column 42, lines 49-50, after "clusters" delete "and re-plated on a human feeder cell, and a colony is selected" and insert --wherein the cluster--.

At column 42, lines 51-53, after "human embryonic stem cell" delete "prior to re-plating the selected human Signed and Sealed this Sixteenth Day of March, 2010

David J. Kappos
*Director of the United States Patent and Trademark Office*